US012751422B2

(12) United States Patent
Russek-Sobol et al.

(10) Patent No.: US 12,751,422 B2
(45) Date of Patent: Oct. 6, 2026

(54) DATA-INFORMED METHOD AND SYSTEM FOR TRACKING THE PERFORMANCE OF AIRBORNE OBJECTS

(71) Applicant: CareBand Inc., Chicago, IL (US)

(72) Inventors: Adam G. Russek-Sobol, Chicago, IL (US); Steven L. Russek, Glendale, WI (US); John D. Reed, Dayton, OH (US); Paul Sheldon, Arlington Heights, IL (US); Jon G. Ledwith, Palatine, IL (US); Sam H. Viesca, Lafayette, CO (US)

( * ) Notice: Subject to any disclaimer, the term of this patent is extended or adjusted under 35 U.S.C. 154(b) by 13 days.

(21) Appl. No.: 18/889,598

(22) Filed: Sep. 19, 2024

(65) Prior Publication Data

US 2025/0098634 A1 Mar. 27, 2025

Related U.S. Application Data

(60) Provisional application No. 63/584,552, filed on Sep. 22, 2023.

(51) Int. Cl.
*A01K 11/00* (2006.01)
*A01K 29/00* (2006.01)
(Continued)

(52) U.S. Cl.
CPC .......... *A01K 11/008* (2013.01); *A01K 29/005* (2013.01); *A01K 45/00* (2013.01);
(Continued)

(58) Field of Classification Search
CPC .... A01K 11/008; A01K 29/005; A01K 45/00; A61B 5/1118; A61B 5/6801; A61B 2503/40; H04W 4/029
See application file for complete search history.

(56) References Cited

U.S. PATENT DOCUMENTS 5,226,061 A 7/1993 Van der Veen
8,961,415 B2 2/2015 Boeuf et al.
(Continued)

OTHER PUBLICATIONS

Willem Bouten et al. A flexible GPS tracking system for studying bird behavior at multiple scales Nov. 28, 2012 Springerlink.com (Year: 2012).*

(Continued)

*Primary Examiner* — Gertrude Arthur Jeanglaude
(74) *Attorney, Agent, or Firm* — John D. Reed

(57) ABSTRACT

A system for tracking the performance of airborne objects and a method of assessing at least one performance metric of the airborne object. For example, the system is used to improve performance of falcons in completing one or more tasks. The system includes an electronic device that monitors key physiological parameters, such as heart rate, body temperature, and activity levels, to provide real-time feedback to the falconer. The device also includes an accelerometer and gyroscope to track the bird's movements and provide information about its orientation and direction of flight. The system utilizes machine learning algorithms to analyze the collected data and provide recommendations for optimizing the bird's performance, such as adjusting its diet or training regimen. By utilizing this technology, falconers can gain a deeper understanding of their birds' performance and make informed decisions to improve their success in completing tasks, such as hunting and aerial pursuit.

20 Claims, 11 Drawing Sheets

(51) Int. Cl.
*A01K 45/00* (2006.01)
*A61B 5/00* (2006.01)
*A61B 5/11* (2006.01)
*H04W 4/029* (2018.01)

(52) U.S. Cl.
CPC .......... *A61B 5/1118* (2013.01); *A61B 5/6801* (2013.01); *A61B 2503/40* (2013.01); *H04W 4/029* (2018.02)

(56) References Cited

U.S. PATENT DOCUMENTS

| | | | | |
|---|---|---|---|---|
| 9,014,975 B2 | 4/2015 | Brashear et al. | | |
| 9,894,885 B2 | 2/2018 | Schab et al. | | |
| 11,112,507 B2 | 9/2021 | Dill | | |
| 2015/0230450 A1* | 8/2015 | Norris | A01M 31/002 367/139 | |
| 2020/0364456 A1* | 11/2020 | Tran | G06T 7/0004 | |
| 2022/0111960 A1* | 4/2022 | Tran | B64D 1/18 | |

OTHER PUBLICATIONS

Gross et al., Flight Test Evaluation of Sensor Fusion Algorithms for Attitude Estimation, IEEE Transactions on Aerospace and Electronic Systems, Jul. 2012.
Kano et al., Head-mounted sensors reveal visual attention of free-flying homing pigeons, Journal of Experimental Biology, vol. 221, Issue 17, Sep. 2018.
Jax et al., Health monitoring in birds using bio-loggers and whole blood transcriptomics , www.nature.com/scientificreports, 2021.
Small, Implantable Heart Rate and Temperature Data Logger, STAR ODDI website (https://www.star-oddi.com), date unknown.

* cited by examiner

TRAIN, TRACK, AND EVALUATE FALCON TELWAH TRAINING AND RACE PERFORMANCE

EMBEDDED MACHINE LEARNING MODEL DEVELOPMENT FOR PERFORMANCE METRICS

830
835
840
845
850

DATA-INFORMED METHOD AND SYSTEM FOR TRACKING THE PERFORMANCE OF AIRBORNE OBJECTS

This application claims the benefit of U.S. Provisional Application Ser. No. 63/584,552 that was filed on Sep. 22, 2023 the entirety of which is herein incorporated by reference.

BACKGROUND

The present disclosure relates generally to using a lightweight inertial navigation system to monitor various performance parameters associated with a bird or other object in flight, and more particularly to fusing and analyzing data acquired from such system in order to improve training and competition-based metrics related to such performance parameters.

The use of traditional ground-based, air-based or telemetry-based approaches with which to track birds and other small objects in flight all suffer from certain shortcomings related to one or more of low accuracy, cumbersome and expensive sensors and related equipment and a lack of performing certain real-time or predictive assessments of various avian movement and performance metrics. For example, many traditional wireless communication architectures are not capable of promptly offloading the generated data to a remote location where the information contained within the data may be put to use, while others can't do it efficiently, often by consuming far more bandwidth or power than needed. Likewise, many traditional wireless communication architectures are incapable of performing long-range signal transmission for compact and lightweight energy-constrained devices.

SUMMARY

With the foregoing in mind, the authors of the present disclosure have developed a system that uses an electronic device that acts as a coordinator for various activities associated with tracking, training and evaluating various metrics related to the flight of birds and other airborne objects. In one form, the system and methods disclosed herein include some or all of the components and associated functionality associated with the electronic device that is disclosed in that US published application and patent.

By using a low-power wide area network (LPWAN)-based approach to communicating acquired data between the network and a wirelessly remote end-use application as disclosed herein, the authors of the present disclosure have found that certain expenses and infrastructural complexities associated with conventional high-bandwidth cellular-based approaches, including those that may use one or more of Long Term Evolution (LTE), Global System for Mobile Communications (GSM), code division multiple access (CDMA), time division multiple access (TDMA), Universal Mobile Telecommunications System (UMTS), General Packet Radio Service (GPRS), Voice over IP (VoIP) or the like, may be reduced or eliminated. Such avoidance is particularly valuable when the system relies upon energy-constrained devices such as the electronic device 100. Similarly, an LPWAN-based approach is beneficial in situations where a balance between the factors range, energy consumption and bandwidth favors the first two over the third. For example, local area networks (LANs) and related high-bandwidth architectures may be difficult to implement over longer ranges and in situations where certain devices (for example, the electronic device 100) within the network are not mains-powered.

According to an aspect of the present disclosure, a method of locating a bird is disclosed. The method includes configuring an electronic device to be adaptively attached to the bird, the electronic device including a microcontroller and a communication module that cooperate together to acquire inertial data, environmental data and physiological data from numerous sensors, as well as to acquire geoposition data from one or both of a terrestrial system and an extraterrestrial system. Upon allowing the bird to become airborne, the method further includes operating the electronic device to convert the acquired inertial, environmental, physiological and geoposition data into flight data of the airborne bird. The method further includes acquiring (or receiving) observational data about behavior of the bird, and further uses the communication module to exchange the flight data and the observational data between the electronic device and an operations center over a communication network. In addition, the method includes analyzing at least one performance metric of the bird based the exchanged flight data and observational data.

According to another aspect of the present disclosure, a method of using machine learning to analyze data collected by a bird training and optimization system is disclosed.

According to another aspect of the present disclosure, a method of using a machine learning model to evaluate a health condition of a bird is disclosed.

According to another aspect of the present disclosure, a system for analyzing the health condition of a bird is disclosed.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

Figure 1:
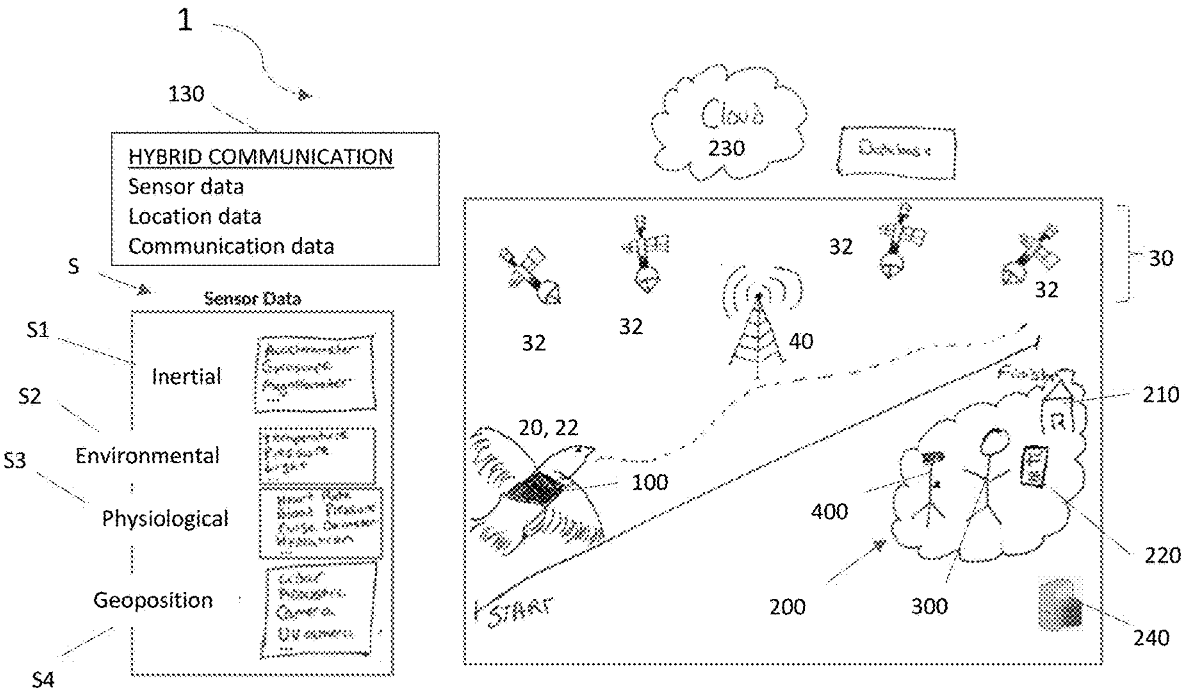
FIG. 1 depicts a simplified view of wireless signal connectivity between an electronic device that is placed on an animate airborne object, a satellite-based extraterrestrial and a ground-based operations center according to one or more embodiments shown or described herein.

It will be appreciated that for the sake of clarity, elements depicted in the drawings are not necessarily to scale, and that certain elements may be omitted from some of the drawings. It will further be appreciated that certain reference numerals may be repeated in different figures to indicate corresponding or analogous elements.

DETAILED DESCRIPTION

The Applicants of the present disclosure have discovered that one technological difficulty to overcome relates to how to sample and analyze various forms of data relating to a bird or other airborne object in the course of a movement-related activity as a way to determine whether such airborne object is functioning in accordance certain expected performance metrics. One part of this difficulty relates to how to how to perform such sampling in real-time or near real-time conditions using lightweight, minimally-invasive sensing equipment, while another part relates to how to fuse the disparate pieces of sampled information into meaningful data. Yet another part of this difficulty relates to how to acquire geoposition data of the airborne object with a high degree of precision during periods of highly dynamic maneuvers. Another technological difficulty to overcome relates to how to perform an analysis on the data in a predictive, forward-looking (rather than descriptive, backward-looking) manner such that potential adverse performance metrics can be identified and corrected before they become too severe. The present technical solution is to provide an electronic device that can aggregate the disparate forms of sensor-, observational- and geoposition-based information using a lightweight, inexpensive platform that in turn can convert the information into a user-intelligible analysis that can be wirelessly conveyed to a user while the movement-related activity of the living organism is in progress.

Referring first to FIG. 1, a bird training and optimization system 1 that is based on data acquired by an electronic device 100 is shown. It will be appreciated that the bird training and optimization system 1 may alternatively be described by other names, such as a bird training and racing system or the like, depending on the usage or arrangement of the various components described herein. It will be further appreciated that choice of the name will be apparent from the context. As shown, the electronic device 100 may be wearable such that it can be secured to an airborne object 20, such as by wearing, affixing or implantation; in such cases, it is referred to herein as a wearable electronic device 100. As shown, the airborne object 20 is animate (such as a bird in general, a bird of prey in particular and a falcon with ever more particularity, collectively bird 22 unless indicated with greater specificity elsewhere). It will be appreciated that the system and methods disclosed herein have applicability to other natural creatures (including those on land and sea rather than in the air), as well as manmade (that is to say, inanimate) objects such as aircraft both manned and unmanned, including drones and robotic aircraft configured to mimic the appearance of an actual bird. In one non-avian example, the electronic device 100 may be applied to a person who is in need of health or location monitoring, making him or her a wearer. In yet another form, the wearer may be a dog, cat, other pet, livestock or the like that may benefit from the positioning, locationing, orientation, geofencing, wireless tracking (including that through tag-based triangulation or the like for either indoor or outdoor use, often with high-bandwidth protocols such as ultra-wideband (UWB) or lidar), alternate reality (AR) or virtual reality (VR) tracking (such as pose tracking, optical tracking, inside-out tracking, outside-in tracking or the like), as well as other capability discussed herein. Accordingly, the term "wearer" or the like may be used herein to identify the object to which the electronic device 100 is affixed. Relatedly, in an inanimate example, the electronic device 100 may be applied to or integrated into a drone, piloted aircraft, unmanned aircraft or other manmade aerial vehicle (all constituting various forms of the airborne object 20) where training for a particular flight path or mission may take place in an automated or partially automated manner, such as through training a machine learning (ML) model that will be discussed in more detail later in this disclosure. In one particular form, some or all of the data acquired for such training (as well as the various forms of data preprocessing, feature extraction, algorithmic training and inference engine operation) may take place in the electronic device 100 as an edge computing device (also referred to herein as an edge-based platform, an edge processing device or more simply as an edge device). Once training of an airborne object 20 is complete, it may be used in an automated manner for competition, location monitoring, hunting or the like. It will be appreciated that in situations where the airborne object 20 in question is not a bird 22, the name of the bird training and optimization system 1 will become correspondingly broader to encompass the name of such airborne object 20, replacing the name "bird" with the respective name, such as "aircraft", "drone" or the like.

In one form, the system may include an operations center 200. The operations center 200 may be any unit, device or combination of devices that is in wireless signal communication with the electronic device 100 such that data received into one can be shared with the other. Regardless of whether the operations center 200 is fully part of the system or merely in cooperation therewith, it will be understood that it may operate solely as a receiver, solely as a transmitter, or as both in the form of a send and receive device, as well as perform at least some of the calculations or analyses necessary to understand or predict performance metrics associated with the bird 22. Thus, in one form, the operations center 200 may be set up as a separate platform (such as shown) at a remote location from the electronic device 100. In one form, the operations center 200 may be a base station 210 or related stationary, ground-based center where the collection of data acquired from the electronic device 100 (and possibly elsewhere) as well as at least some of the processing of such data into analytical insights takes place. In one form, the base station 210 may include physical building structure that can house—among other things—communication and data processing equipment. In another form, the operations center 200 may be a portable device 220, such as a tablet, smartphone, portable computer or related mobile platform such as that presently shown being held by an individual (also referred to herein as a user) 300 who is associated with the bird 22. Regardless of whether the operations center 200 is configured as a portable or stationary platform, it can in one form be configured to handle various control and communications functions, as can the electronic device 100 in situations where some or all of the analytic functions are capable of being performed thereon. In one form, the operations center 200 may be configured as a master control center in order to not only receive direct signals from the various satellites 32, but also to coordinate with one or more of the other components depicted in FIG. 1 to improve the positional accuracy determinations of the bird 22 or other airborne object 20 of interest that will be discussed in more detail as follows with regard to signal error reduction.

It will be appreciated that the types and scales of measurement of the acquired data is potentially voluminous. For example, some forms of the data may be quantitative, while others may be qualitative. The quantitative data may be broken down into increasing degrees of granularity, such as into discrete or continuous data the latter of which may be further broken down into interval scale data or ration scale data. Relatedly, the qualitative data may be broken down into increasing degrees of granularity, such as into nominal nonnumerical nominal data and nonnumerical ordinal data. The understanding which types of data are being worked upon by the one or more parts of the electronic device 100 or other parts of the bird training and optimization system 1 helps in various fusing and ML activities as discussed herein.

Within the present disclosure, the individual 300 who is associated with the bird 22 may be any person who is tasked with collecting and analyzing various forms of the data that is acquired from the electronic device 100 that is turn acquires data from—among other things—one or more of the sensors S. Such individual 300 may be a bird owner, a bird trainer, medical personnel, race fan, user of one or more parts of the system or the like all of whom may have an interest in assessing one or more performance metrics associated with the bird 22. In situations where the individual 300 needs to correlate the acquired data with broad observational sensor-informed categories of data, he or she may use static or general metrics (or categories) of the bird 22. These general metrics may be broken down into more specific behavioral or physiological states, that in turn may be broken down further to describe (for example) the exact behavioral manifestations of a particular state. To use a human analogy, the static or general metrics may include broad health and wellness categories that correspond to general health (such as body mass index (BMI), blood pressure, general mood states, living conditions, age, gender, diet, habits, sleep patterns or the like). Broken down in a different way, physical health metrics may include general health such as BMI or blood pressure, while mental health metrics may include general mood states and diagnosed conditions. Health may also be put into an environmental context where factors such as living conditions, exposure to pollutants or the like are significant. Relatedly, demographic information such as age, gender and lifestyle metrics (such as diet, exercise habits or the like) may be used. More specific behavioral or physiological states may include specific health states (such as feeling stressed, feeling anxious or the like), physical health states (such as experiencing fatigue), mental health states (such as feeling stressed) and lifestyle states (such as experiencing the effects of a new diet (such as Ketogenic or Paleolithic), muscle soreness from exercise or the like) may all be categorized, classified or otherwise understood, such as through the machine learning or algorithmic approaches discussed herein. Moreover, manifestations of a particular state (that is to say, observable behaviors or symptoms) may include increased heart rate, sweeting, irritability, nail-biting or the like) that has as examples (just to name a few) (i) physical fatigue such as slowed movements or yawning, (ii) stress that may be reflected in increased heart rate, sweating and (iii) effects of a new diet such as dizziness, constipation or the like. In one form, this conceptual understanding of the interaction between the acquired data and observational sensor-informed categories of data (such as through the use of biomarkers and physiological data) can be used to provide an overall health metric encompassing both of these forms of data. As noted, the generation of intelligence in the form of diagnostics, predictive analytics based on the data may be understood through the use of ML, either at the edge in the form of the electronic device 100, centrally at the operations center 200 or other backhaul, or a combination of both edge and centralized processing and analysis.

As will be discussed in conjunction with the fusing of data from the various sensors S (such as geoposition data, inertial data, physiological data and environmental, just to name a few), indicia of certain forms of behavior (such as stress, fear, frustration and overheating) may be correlated with the observational behavior (such as by a trainer or other knowledgeable observer) that includes—as previously mentioned—bird 22 species, age of the bird 22, prior training regimens, information related to diet, health metrics, weather conditions at the time of observation, migration patterns, social interactions, mating habits, nesting behavior, foraging strategies or the like) in order to have a more holistic understanding of the bird 22.

In one form, the individual 300, through prior knowledge, experience, training or the like, may optionally input into the operations center 200 observational data known specifically to him or her. This data (some of which is shown in FIG. 5B) may include bird 22 species, age of the bird 22, prior training regimens, information related to diet (including caloric intake for that day), health metrics, weather conditions at the time of observation, migration patterns, social interactions, mating habits, nesting behavior, foraging strategies or the like. Such input can be through known means, such as typed (keyboard) input or spoken word input (such as a voice message or the like). In one form, this observational data can form the basis of input data to one or more ML algorithms or approaches as discussed herein to convert this data into weights into a final trained ML model. In one form, the observational data can be either quantitative (that is to say, numerically continuous or discrete) or qualitative (that is to say, ordinal or nominal based on perception or the like). In one form, the data that is received by or otherwise input into the operations center 200 may be stored, processed and analyzed locally on the portable device 220, while in another at the base station 210 or other backhaul either of which may contain or otherwise be made cooperative with computational resources such as cloud 230 (which itself may be constructed as numerous interconnected nodes), servers 240 or other known computing platforms. In any event, this enables the receipt into the electronic device 100 of the observational data about behavior of the bird 22 from an individual with specialized knowledge about such bird. In situations where some or all of the sensor S data (as well as geoposition data that will be discussed as follows) is acquired, processed or analyzed by the electronic device 100, the observational data that has been received into the portable device 220 from the individual 300 may be wirelessly conveyed to the electronic device 100 from the operations center 200 such that additional analytical operations may be performed thereon. As with the operations center 200, in one form, the backhaul may optionally form part of the system, while in another it is merely made to be cooperative therewith.

The electronic device 100 collects, processes and analyzes geoposition, inertial, environmental and physiological data related to the airborne object 20 in order to determine flight-based information such as the position, movement, path, direction, route, pattern, course made in space or related indicia of such flight. Within the present disclosure, geoposition data is that in which the location and movement of the airborne object 20 is known within a global framework through recourse to coordinates, landmarks or other reference point or points through various means. As such, the term "geolocation" is understood to form a subset of geopositioning in that it employs various forms of local or remote data collection (such as from the electronic device 100, operations center 200 or the like) in order to determine the location of the airborne object 20, either within the global framework or within a more arbitrary portion thereof. In one form, such geoposition data also includes time data, such as through timestamping or that which can arise of various clock synchronization activities. The acquisition of such time data, whether as part of the inclusion into the geoposition data or independently therefrom, will be apparent from the context. It will be appreciated that when the airborne object 20 is an inanimate object such as a drone or other aircraft, certain forms of data that may be germane to the bird 22 or other animate object 20 (for example, physiological data) are not needed. In an analogous manner, actual data being acquired for such an inanimate airborne 20 may include that pertaining to the operational status of one or more of such object's components, modules, systems, subsystems or the like. By way of non-limiting example, monitoring of engine operation, remaining onboard fuel, aerodynamic or other structural loading of the airframe or the like.

In one form, the geoposition data may be acquired in various ways, including through one or more extraterrestrial terrestrial systems 30 that are in signal communication with the electronic device 100. An example of such an extraterrestrial system 30 may include a global navigation satellite system (GNSS) in general or the well-known global positioning system (GPS) in particular, in either event including includes a set of satellites 32 that determine the latitude and longitude position of the electronic device 100 on earth through well-known methods. In one form, the geoposition data is accompanied by time measurements so that precise event recordation, sequencing, clock synchronization and related temporal-based accuracy enhancements may be realized. In one form, precise point positioning may be achieved by augmenting traditional GPS (with its need for backward compatibility) with a high accuracy and robustness service (HARS) in order to reduce errors associated with satellite orbit and clock timing, as well as ionospheric and tropospheric signal propagation distortions. Approaches such as this may also offer enhanced signal transmission security through encrypted messaging or data signing. In one form, the ML model discussed herein may be used to further at least some of these errors, such as the ones related to ionospheric signal propagation distortions.

In situations where the airborne object 20 is bird 22, the acquired data may be used for assessing figures of merit in the form of performance metrics for training (for example, hacking that involves a sequence of procedures that includes captivity, releasing, flight and recapture, or the time it takes to traverse a course, track or other measurable distance) or real-time activities (such as that used in a sporting event or related competition, health monitoring, aviculture or the like). Moreover, the functionality of the electronic device 100 allows the data to be used for edge-based predictive analytics, including that associated with creating or operating a ML model 800 or related inference engine that will be discussed in more detail in conjunction with FIGS. 8A and 8B. As will be discussed in more detail as follows, one or more sensors S used to acquire at least some of the data associated with bird 22 performance metrics may themselves be local (that is to say, on or adjacent the bird 22, as shown) or remote (such that their sensed information is acquired at a distance from the bird 22). Within the present disclosure, the term "sensors" will be understood to apply to those that are both shown and described generally (as indicated by sensors S), as well as those that are particularly identified with more particularity and that will be discussed in more detail as follows. It will be understood that when discussing the airborne object 20 in general, the term "geoposition data" will apply to such object, whereas when discussing the bird 22 in particular, the term will be referred to as bird geoposition data.

In addition to the cooperation with the extraterrestrial system 30, the electronic device 100 may also either include or otherwise be signally cooperative with a terrestrial system 40 (also referred to herein as a ground-based augmentation system). Examples of terrestrial systems 40 may include a real-time kinematics (RTK) system 400 (that will be discussed in more detail as follows), a mobile telephone, one or more beacons (such as through triangulation, trilateration or the like where numerous beacons cooperate together), as well as through more conventional means such as visually, through the use of cameras, radio-frequency measuring devices (radar, lidar or the like), in addition to manual methods of data gathering such as through a map or celestial navigation, or electronic methods of position lines, position circles or the like. This and other forms of data may be fused by the bird training and optimization system 1 (generally) and the electronic device 100 (particularly). For example, one form of data fusion that may take place includes a computer program product formed by a computer-readable medium and program code that can compare known mapped information (in either two-dimensional or three-dimensional space) about a particular terrestrial location to image-acquired data from the bird 22 to assist with location determination, navigation or other information about the flight pattern, performance metrics or the like. In one form, this acquisition, fusing, analysis and reporting of the desired information is performed in real-time, and may be accompanied with still or motion-based video updates from or about the bird 22. As will be discussed in more detail elsewhere, one form of data fusion relates to the voluminous amount of data that is being acquired by the various sensors S. This version, called sensor fusion, will help to render the information that is produced from sensors S of different data types, source of manufacture, signals, formats and functionality into a form more suitable for edge-based ML processing. Such fusion may be performed in one of numerous ways, such as knowledge-based, probabilistic and statistical, for example).

In one form, the terrestrial system 40 may employ cameras, imagers or related visual acquisition means in order to making positioning determinations of the bird 22 or other airborne object 20 being monitored. In one form, the terrestrial system 40 may include additional equipment for even more accurate positioning. Examples of such accuracy-improving approaches may include antenna diversity features (including orthogonal antennas, isotropic radiators, omnidirectional radiators, dual antennas or the like) as a way to reduce multipath effects. Moreover, other approaches (such as optical inertial odometry) may be used in situations where GNSS signals are unavailable (also referred to herein generally as a communication-deprived environment and more particularly as a GPS-deprived environment). In this way, the terrestrial system 40 helps to improve the accuracy of the acquired data from the extraterrestrial system 30 that may have been compromised by factors inherent in ionospheric or tropospheric propagation, as well as multipath effects. Still other approaches may include local area augmentation system/ground based augmentation system (LAAS/GBAS), differential GPS (DGPS) or dual-band GPS, as well as the use of specialized antennas, such as Yagi-Uda directional antennas, hybrid GNSS and IMU antennas or the like. All such accuracy-improving approaches are within the scope of the present disclosure. In one form, the terrestrial system 40 may be in signal communication with the operations center 200 such that information acquired by one may be conveyed to the other, either directly or indirectly the latter of which could be through the electronic device 100. In another form, the terrestrial system 40 and the operations center 200 may be physically or functionally integrated with one another. In one form, the terrestrial system 40 may function as a GNSS or GPS reference station that can perform clock and orbital calculations as well as perform atmospheric model calculations. All such forms of signal sharing and communication cooperation are deemed to be within the scope of the present disclosure.

The RTK system 400 is one form of an accuracy-improving approach. In particular, the RTK system 400 uses a four-part accuracy enhancement approach that includes (1) establishing a direct line of signal communication between satellites 32 of the extraterrestrial system 30 and the airborne object 20, (2) establishing a direct line of signal communication between the satellites 32 of the extraterrestrial system 40 and the ground-based RTK system 400, (3) establishing a direct line of signal communication between the terrestrial system 40 and the operations center 200, and (4) establishing a direct line of signal communication between the operations center 200 and the bird 22 or other airborne object 20. In one form (as shown) the terrestrial system 40 is itself either in signal communication with equipment that makes up operations center 200 or (as previously mentioned) forms a part thereof, and that regardless of the physical integration or location of one relative to the other, all forms are deemed to be within the present disclosure. As with other components discussed herein that may have differing degrees of physical and location integration with one another, the communication tower will be understood to form part of one or both acting as a ground-based receiver asset for one or both of the extraterrestrial and terrestrial systems 30, 40, depending on the configuration and regardless of the degree of physical connection or proximity. The use of the data collected by one or both of the communication tower and the RTK system 400 is included to correct for the various errors that are introduced into the satellite 32 signals; this in turn improves the roughly accuracy of traditional GNSS measurements, such as from roughly a meter to roughly one centimeter. It will be appreciated that RTK system 400 is mentioned as a non-limiting example, and that the use of one accuracy enhancement approach rather than another may be based on the particular environment in which the electronic device 100 is used, including whether the correcting signals need to be uninterrupted, the need for real-time analysis, location of one or more system components or the like. In configurations where the RTK system 400 is used, yet further accuracy may be achieved through networks or clusters. In one form, some or all of the satellites 32, terrestrial system 40, operations center 200 and RTK system 400 may be made to augment a GPS signal as a way to achieve the aforementioned precise point positioning.

In one form, the generation of performance related metrics, predictive analytics or other indicia of the health, performance or other measure of the bird 22 arising out of the use of the training and optimization system 1 that is based on data acquired by the electronic device 100 may correspond to a correlative system such as that known from statistical mechanics. In such case, a correlation function is a measure of the order in a given system, as characterized by a mathematical correlation function. Correlation functions describe how granular variables (such as the various forms of acquired independent data) are related. For the purposes of the present disclosure, the given system may correspond to the bird 22 or other airborne object 20.

Figure 2:
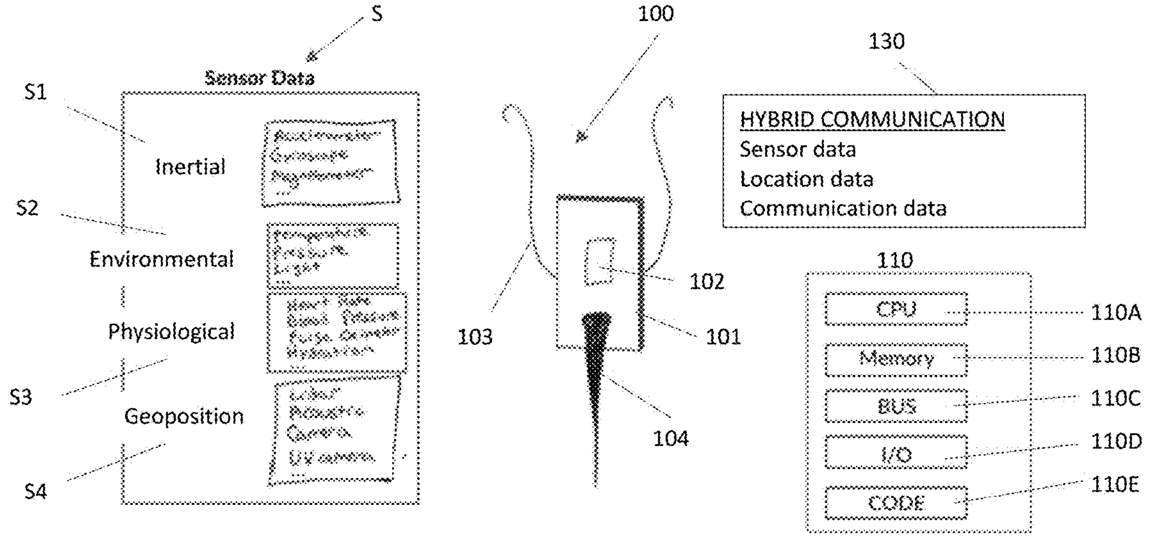
FIG. 2 depicts an exploded view highlighting details of the electronic device in one form factor.

Referring next to FIG. 2, details associated with the electronic device 100 are shown in a block diagrammatic view along with sensors S that, as noted elsewhere, may or may not be situated in or on the electronic device 100, depending on packaging or other needs. As can be seen, the electronic device 100 includes numerous electronic components that make up its power, sensing, communication and processing functions. The sensors S may include an inertial measurement unit (IMU) $S_1$, one or more environmental sensors $S_2$, one or more physiological sensors (also referred to herein as biosensors) $S_3$ and one or more geoposition sensors $S_4$ such as visual sensors such as cameras, other optical (lidar, monocular camera, UV camera, optical flow sensor) acoustic sensors such as microphones, in addition to compasses, altimeters or the like that are discussed in U.S. Pat. No. 11,147,459 entitled WEARABLE ELECTRONIC DEVICE AND SYSTEM FOR TRACKING LOCATION AND IDENTIFYING CHANGES IN SALIENT INDICATORS OF PATIENT HEALTH that is owned by the Assignee of the present disclosure and the entirety of which is incorporated herein by reference to the extent that such incorporation does not cause incompatibilities with the present disclosure. In one form, the sensors S may form a part of a grid, including as an embedded sensor network that includes dedicated computing functionality. Likewise, the various sensors S, computational assets and other components disclosed herein can form either a unitary or distributed architecture such that one or more of the recited sensors S, computational assets and other components can part of a larger package, assembly or system, or can be separated from (but still cooperative with) one another. By way of example, in one form the electronic device 100 may be thought of as containing numerous disparate, relatively discrete components, systems, modules or the like that are distinct from one another by their particular components, functionality or construction, while in another as a unitary whole, such as in situations where some of the components, functionality or construction share common resources such as housing or packaging, circuitry, memory, power sources or the like. Relatedly, the equipment that is used on the electronic device 100 for performing various algorithmic, analytical and related computational tasks may itself be described as either a single, unitary device or as a collection of distinct (albeit coordinated) components. As noted elsewhere, the operations center 200 may be similarly understood to define a unitary or distributed architecture, depending on factors such as packaging space, functional needs, modularity or the like of the corresponding base station 210 or portable device 220. It will be appreciated that—semantics aside—all forms of unitary, distributed or hybrid architectures of these and other systems, sub-systems or the like are deemed to be within the scope of the present disclosure.

In one form, the sensors S and the electronic device 100 may form the basis of a so-called smart system where internet of things (IoT)-based data collection, processing and wireless communication of sensor data representing at least one of inertial conditions, environmental conditions and physiological conditions of the bird may be used to provide data-informed insights into flight path information, performance metric or other information about the bird 22. In one form, ML techniques may be used to provide data-informed predictive analytics about the bird 22. Such techniques may include one or more of random forests, bagged trees, decision trees, boosted trees, long short-term memory (LSTM) networks, support vector machines (SVMs), logistic regression, naïve Bayes, memory-based learning, neural networks (including deep learning, convolutional neural networks (CNNs) or feedback-based recurrent neural networks (RNNs) or the like), clustering approaches (such as k-means clustering, hierarchical clustering or the like). Likewise, graph-based algorithms as well as anomaly detection (such as one-class SVM, isolation forest, local outlier factor or the like) may be used. As discussed elsewhere, inferences (such as those run on the trained ML model 800 and including various forms of prescriptive analytics) may be performed at the edge on the electronic device 100, on the cloud 230 or other backhaul, depending on the need. In a related manner, at least some of the other steps (such as the preprocessing, feature extraction and training of the acquired data that are discussed in more detail in conjunction with FIGS. 8 and 9) needed to generate data-informed insights may be performed at either the edge or somewhere in the backhaul. The data collected from the sensors S (as well as the geoposition data and observational data) may be used in furtherance of various training-based or competition-based activities. In one form, such data may be accessible to the individual 300 or other interested person in a relatively agnostic or autonomous form, such as through the use of semantic layers or other forms of relational structure-free querying that promote ease of use by such individual 300. This form of data arrangement (which may be made available from one or more forms of the aforementioned preprocessing or related cleansing) is particularly useful in IoT-based data use scenarios. In another manner, generative AI may be used on the acquired data to provide prescriptive analytics or instructions on what to do next. Such approaches may include natural language processing (NLP), graph-based algorithms, large language models (LLM) or the like.

In one form, the electronic device 100 includes a housing 101 that acts as a platform to support other components. In one form, a light-emitting diode (LED) 102 may be mounted on a surface and connected to circuitry inside the housing 101 to selectively display indicia of interest, such as a "power-on" status or the like. A securing mechanism 103 (shown presently as a wire with fastenable opposing ends, but understood to possess different form factors, depending on the size, shape or related attribute of the airborne object 20 or bird 22) promotes ease of mounting. An antenna 104 may be disposed in or on the housing 101. It will be appreciated that the form factor of the electronic device 100 and its various components is exemplary only, and that other form factors that have more, fewer or different construction (including those for packaging of the various components within), as well as differing degrees of packaging rigidity, are also contemplated. As such, form factors that can be tied, adhered, clipped or otherwise affixed on the body of bird 22 are also within the scope of the present disclosure. In one form, the components include a microcontroller 110, battery 120 and a wireless communication module 130 one or more of which may be placed on a common substrate such as printed circuit board 140. Although not shown, in one form the electronic device 100 may include a display such as a graphical user interface (GUI) or other means for conveying visual information, particularly if it is configured as a low power variant such as an electrophoretic display, electronic ink (E ink), intelligent paper or the like. Such display may be either in place of or in addition to the LED 102. In one form, the microcontroller 110 (as well as other components) may be configured as an embedded system such as a system-on-chip (SoC) that itself forms an integrated circuit that may include memory and one or more peripherals for executing instructions. In one form, embedded architectures promote the ability of the electronic device 100 to provide edge-based inference engines for real-time or predictive analytics. In one form, the microcontroller 110 includes one or more processors 110A, memory 110B, bus 110C, input/output 110D (possibly for use as part of a user interface) and machine code 110E. Additional components (not shown) may include one or more filtering mechanisms (such as amplifiers, limiters, modulators, demodulators, data transmission signal conditioners, analog-to-digital and digital-to-analog converters or the like), as well as a power management mechanism. In one form, the microcontroller 110 itself may be described as either a single, unitary device or as a collection of distinct (albeit coordinated) components. As such, in situations disclosed herein that employ the microcontroller 110 to specifically perform algorithmic, analytical and related computational tasks (including those responsive to instructions from the machine code 110E), it will be understood that the majority or entirety of such computational activity takes place within the processor or processors 110A, unless the context clearly recites otherwise. Likewise, in one form, the bus 110C—which signally couples various system components to one another—may be of numerous types, including a local bus, a peripheral bus, a memory bus, an accelerated graphics port or the like using one of numerous bus architectures such as an Industry Standard Architecture (ISA) bus, a Peripheral Component Interconnect (PCI) bus, a Micro Channel Architecture (MCA) bus, an Enhanced ISA (EISA) bus, a Video Electronics Standards Association (VESA) local bus or the like. In one form, the microcontroller 110 is formed out of multiple chips within a chiplet-based architecture. In one form, the microcontroller 110 is based on an open standard ISA such as RISC-V to provide flexible, modular designs. In one form, the microcontroller 110 is configured as a low-power SoC (including with power management features) as a way to extend the life of the battery 120.

As previously noted, the electronic device 100 provides a technical solution by aggregating the disparate forms of acquired sensor-based and geoposition information such that this information can then be converted into user-intelligible analysis. As will be discussed in conjunction with FIG. 5B, this may include converting the acquired inertial, environmental, physiological and geoposition data into flight data of the airborne bird, such as through fusion of the various disparate forms of data. Such converting may include one or more of data preprocessing, processing, model generation or training, as well as use of the ML model 800 to produce an inference. It will be appreciated that in certain situations, the flight data may be the raw data that undergoes little or no local conversion (that is, conversion that takes place on the electronic device 100 prior to being transmitted to a remote location such as the operations center 200). Likewise, it will be appreciated that in other situations, the flight data may be that which has undergone complete or substantially complete local conversion on the electronic device 100 prior to being transmitted to such remote location. Furthermore, it will be appreciated that in still other situations, the flight data may be that which has undergone a moderate amount of local conversion on the electronic device 100 prior to being transmitted to such remote location. Thus for example, upon allowing the bird 22 to become airborne, the operation of the electronic device 100 may or may not include converting some or all of the acquired inertial, environmental, physiological and geoposition data into a different form prior to being conveyed to a remote location using the communication module 130. As such, the form, content or related nature of the flight data disclosed herein will be apparent from the context.

By way of non-limiting example, the IMU $S_1$ includes separate sensing units, including accelerometers (to measure linear acceleration), gyroscopes (to measure angular (that is to say, rotational) velocity) and magnetometers (to measure magnetic dipoles and fields) in order to attain 9-degreee-of-freedom (DOF) inertial data that corresponds to three DOF for each of the major axes in a Cartesian coordinate system in Euclidean space. As with the microcontroller 110 of FIG. 1, the IMU $S_1$ may be configured either as an SoC or as a group of disparate components, and that either architecture is within the scope of the present disclosure. In one form, the IMU $S_1$ performs its own fusion of the accelerometer, gyroscope and magnetometer measurements such that the output produced is in the form of a stable orientation within three-dimensional space. In one form, the IMU $S_1$ may be deemed to be the substantial equivalent of a position-based 6-DOF device (that provides the roll, yaw and pitch of rotational movement and the forward, backward, up, down and lateral components of translational movement) along with the addition of the magnetometers to provide some measure of orientation and in turn full 9-DOF functionality. Regardless of whether the sensing comes from single, integrated units such as the IMU $S_1$, disparate sources (such as a distributed sensor network or architecture, including those local to the object being monitored, as well as those that are remote relative to the object, such as the GNSS-based signals or the like) or a combination thereof, they may all cooperate with or be a part of the system in order to provide the data needed to analyze the performance metrics of the bird 22. All such variants are deemed to be within the scope of the present disclosure, as are devices that may include additional sensors, such as altimeters that measure barometric pressure or the like. In one form applicable to the present disclosure, the IMU $S_1$ may be based on a microelectromechanical systems (MEMS) architecture in order to accurately track the roll, yaw and pitch data that corresponds to orientation of the bird 22 in space. In one form, the IMU $S_1$ can provide dead reckoning information (such as current position, heading, speed, acceleration turn rate or the like based on a known position prior in time along with present position, speed heading and time), as well as be coupled with the extraterrestrial system 30 to have both inertial navigation system (INS) and GNSS functionality. In this way, an absolute orientation in Cartesian space may be determined.

In one form, the microcontroller 110 may process, analyze and digitally filter data from each of the extraterrestrial system 30 and IMU $S_1$ in order to enhance or adjust inertial attitude, position and velocity estimates, including but not limited to correcting biases that may have found their way into accelerometer gyroscope measurements.

The environmental sensors $S_2$ may include those that can measure weather (such as temperature, wind speed, wind direction, humidity (including one or both relative and absolute), precipitation or the like) local terrain (such as whether it is an open field, a dense forest, mountainous or the like, all as a possible influence on the ability of the bird 22 to locate and track prey), light (such as solar irradiance or the like), air quality (for pollutants such as agricultural pesticides, industrial chemicals or the like) and noise (which can disrupt hunting and feeding behavior of the bird 22). In one form, one or more of the environmental sensors $S_2$ may be physically situated on the electronic device 100, while in another, one or more may be situated elsewhere, either on the bird 22 or remotely, but in either event configured to collect the particular type of data for which they were designed, as well as to communicate the collected data to the electronic device 100. As such, in one form, the environmental sensors $S_2$ may form a capacitive sensor array, including those based on a flexible, adhesive substrate or other form factor that is readily affixable to the bird 22, while in another formed as part of the electronic device 100. Changes in local environmental conditions may impact accuracy of data that is being acquired by the various sensors S. As such, by measuring various ambient parameters (such as temperature, wind speed, wind direction, humidity, solar intensity, precipitation or the like), the data acquired by the environmental sensors $S_{2,}$ may be processed in order to calibrate the other sensors S to correct for errors in such other measurements, including those related to bias, scale factor, misalignment, gyroscopic g-sensitivity or the like.

The physiological sensors $S_3$ may include those that can measure numerous biological parameters such as cardiovascular (including heart rate), respiratory (including blood oxygen, respiration rate or the like), white blood cell count, gastro-intestinal, body temperature, glucose saturation, Galvanic Skin Response (GSR), Electroencephalography (EEG), Electrooculography (EOG), Electrocardiography (ECG), blood pressure, spirometry, pulse oximetry, hydration, lactate, biomarker sensors or the like. In one form, the physiological sensors $S_3$ may form a capacitive sensor array, including those based on a flexible, adhesive substrate or other form factor that is readily affixable to the bird 22. Likewise, one or more of the physiological sensors $S_3$ may be formed as part of the electronic device 100. In one form, and as with the trainer observational data, the sensed data from the physiological sensors $S_3$ (possibly in conjunction with the sensed data from one or both of the IMU $S_1$ and environmental sensors $S_2$) may act as biomarkers that can provide indicia of bird 22 behavior such as stress, fear, frustration, overheating, disease, malnutrition, heat stress and dehydration any one of which may themselves manifest itself in either quantitative or qualitative terms, as will be discussed in conjunction with FIG. 7. In one form, the physiological sensors $S_3$ may be wither worn on or implanted in the bird 22 to be used for bio-logging or related ways to determine bird 22 health based on the measured biological parameters. Within the present disclosure, the physiological sensors $S_3$ may include suitable electronic components such as a transducer in order to convert the measured biological response into a suitable electrical, optical or other signal that in turn is processed by the microcontroller 110. Moreover, the terms "physiological" and "biological" may be construed interchangeably in the present disclosure unless the context-related specificity dictates otherwise, for the purpose of describing various biological parameters and functions associated a living organism that may be sensed or otherwise measured by the physiological sensors $S_3$. Furthermore, when the physiological properties being acquired are of the bird 22, they may be referred to herein as "bird physiological data" or variants thereof.

In one form, the memory 110B may contain data structures, program code, machine code 110E, native instruction sets, computer-readable instructions or the like such that upon loading the program code 110E into memory 110B, the program code 110E may execute one or more steps in a manner consistent with the methods disclosed herein. In one form, such data structures may be in the form of charts, databases, equations, functions, graphs, lookup tables or the like that may be stored in or otherwise accessed by memory 110B for use by the processor or processors 110A to perform the various computational and predictive tasks disclosed herein. As such, the program code implemented on a computer-readable medium forms a computer program product that is configured to carry out one or more of the functions, steps or other parts of the methods described herein, including a substantial entirety of such methods. As previously mentioned, such a computer program product may include the aforementioned one that performs data fusing to provide visual or other forms of position determination for the bird 22 or other airborne object 20 of interest.

The battery 120 may exist in any form function to promote ease and durability of attachment to the bird 22 or other airborne object 20. Thus, coin cells, conformal arrays or other shapes, sizes and weights may be chosen, depending on the energy capacity, size of the bird 22 or the like. In another form, the battery 120 may be replaced or supplemented by a passive energy source such as solar power through photovoltaic panels or through energy harvesting such as from wing flapping from the bird 22.

As previously noted, in one form the electronic device 100 is configured as an edge device that can perform the various data acquisition and analytic processing and analysis (including as an inference engine that performs predictive analytics) in an autonomous (that is to say, no input from a backhaul computer system) manner so that recourse to computational backhaul isn't required. This in turn can improve one or more of real-time analysis and response, system cost and complexity or the like. In other forms, various interactive communication between the wireless communication module 130 of the electronic device 100 and a backhaul (which may be either cooperative with or form a part of the operations center 200 as shown in FIG. 1) may be used in order to divide up the various data acquisition and analytical activities. The electronic device 100, either in its capacity as an edge-based platform or as part of a larger system that may include remote, backhaul-based computing resources, is capable of performing predictive analytics based on the various forms of sensed data disclosed herein. Such predictive analytics may include understanding the onset of an infectious disease or other adverse health condition or a change in the bird's behavior.

As with the physical integration and location of the terrestrial system 40 and operations center 200, the sensors S may either formed as part of the electronic device 100 to be integrated therein or be merely in signal cooperation therewith, and that both of these forms, as well as combinations thereof, are deemed to be within the scope of the present disclosure. Relatedly, the sensors S in one form make up a part of the system, while in another are merely cooperative therewith (either directly or through an intermediary communication mechanism) such that the data they collect may be processed and acted upon by the electronic device 100 or elsewhere, such as in computational backhaul that is in communication therewith either directly or through an intermediary such as the operations center 200. Both of these forms, as well as combinations thereof, are deemed to be within the scope of the present disclosure. In one form, one or more of the sensors S may be placed elsewhere on the bird 22, while in another form elsewhere on the electronic device 100 (such as on a separate chip, printed circuit board (PCB) or the like), while in still another at a remote location such that the data they collect may be conveyed to the electronic device 100 either through known wired means or wirelessly through one or more of the sub-modules of the wireless communication module 130. In that way, the system collects and fuses various forms of sensor S data as well as position or location data from one or more of extraterrestrial and terrestrial systems 30, 40. Within the present disclosure, the term "position" is understood to be used interchangeably with "location", although the context will make it apparent when situations where greater degrees of precision, particularity or exactitude are required. Likewise, inertial data is that in which the location and movement of the bird 22 or other airborne object 20 is known within a local framework through recourse to sensor-based information, such as that available through the aforementioned IMU $S_1$.

Within the present disclosure, the fusing of the acquired data (such as through a sensor fusion algorithm in particular or a fusion algorithm in general, such as when data from other means such as geoposition data or observational data, either with or without sensor data, is being used) is that which is performed to convert disparate pieces of such data into a form that abstracts the data away from the device that acquired it in order to make it easier to process it by the electronic device 100 or some other part of the bird training and optimization system 1. The types of sensor fusion algorithm arise out of the way the data is operated upon. Thus, one form of fusion may depend on where such fusion is taking place (for example, at the edge, in the cloud or other part of the backhaul, or somewhere else), while another by how much competition there is from various sensors that may be acquiring the same information (that is to say, redundancy of certain sensors), while still another relates to the abstraction level of the data (that is, at what stage should the data be combined).

In one form, the abstraction of the data may take place over various layers, including a sensor S layer that processes the raw sensor data, typically of the same attribute (that is to say, when the sensors S are redundant), a feature layer to extract feature vectors or related representations (where, for example, where sensors are used cooperatively for different modalities) and a decision layer that performs feature classification (for categorical output) or regression (for continuous output). It will be appreciated that the choice of which of these different layers of fusion to use may depend on various factors, such as using the ML model 800 of FIG. 8, the size, complexity or homogeneity of the data, where such fusion is to take place, or other factors. As with differing layers, sensor S fusion may take place over numerous levels, including those for source preprocessing at the signal level, a level for performing spatio-temporal object refinement, a relationship-establishing level between the classified and identified objects, an impact assessment level and a resource management level. By way of a non-limiting example, an architecture that need not know about the particulars of a particular sensor selected from a wide range of disparate sensors is beneficial when the sensors S are competitive or redundant, such as performing the same sensing function (that is, detecting the same property of interest) but sourced from different suppliers, vendors or manufacturers, or across different versions or generations of the same sensor from the same supplier, vendor or manufacturer. In yet another form, and considering the sensing to take place at a perception layer such that a network layer may act as an intermediary with an application layer, the conveyance of the various types of data may be through a set of instructions in the form of an application programming interface (API). One form of software interface that can be used in the control or management of a network of sensors S is a sensor abstraction layer in order to facilitate a unified interface to all of the sensors affiliated with the electronic device 100 or other parts of the bird training and optimization system 1, such as for time-stamping spatio-temporal data as well as the recordation of such data. In one form, the sensor abstraction layer may be embodied in an application-specific integrated circuit (ASIC). In this way, sensor S signals that are received by the sensor abstraction layer become converted into a common form irrespective of the way each of the disparate sensors S acquires, stores, processes or otherwise manipulates the data. Such conversion may take place through cleansing, normalization or other forms of preprocessing. In one form, preprocessing signal data that is acquired from the sensors S can then be subjected to data analysis (that is to say, bird 22 movement or other forms tracking) prior to presenting such data to the individual 300. By way of non-limiting example, the preprocessed signal data may be broken down in order to reduce the complexity of more holistic movements into more discrete head, leg, wing or other body part movements that represent an action taken by one or more such parts. It will be understood that such breaking down may be achieved by other methods as well, such as through a trained ML classifier or regression model. It will be further understood that additional steps to perform sensor S calibration may also be used.

This ability to fuse the data in turn helps provide an architecture for the management of the sensors S and other data-gathering resources even when the nature of the different data types would otherwise not lend itself to such fusing. Furthermore, providing such a mode of presenting the data allows for easier extraction so that the data of a common recognition event being reported by numerous sensors S can be reconciled within the electronic device 100, whether when used in an ML mode of operation or in a more conventional rules-based mode of data processing. One example of providing meaningful intellectual content from such fusion includes determining a location or flight path of the bird 22. It will be understood that this is by example only, and that one or more performance metrics or other forms of interest are also contemplated. As will be discussed in more detail as follows, the sensor fusing algorithm may be based on the aforementioned ML model 800 some or all of which can be performed the electronic device 100 as an edge-based platform such that recourse to the operations center 200 or other computational backhaul is not required.

In one form, the wireless communication module 130 has hybrid communication capabilities through the inclusion of various sub-modules made up of a first sub-module 130A to selectively receive data one or more sensors S, a second sub-module 130B to selectively receive location data in the form signals from one or both of an extraterrestrial system 30 and a terrestrial system 40, as well as third sub-module 130C to communicate signals using LPWAN to provide position, orientation, attitude, movement and related indicia (and optionally edge-based processing and related analysis of such data) of the bird 22 based on acquired data from the other two sub-modules 130A, 130B as well as optional observational data such as that entered into or otherwise acquired by the portable device 220 or other part of the operations center 200. Within the present disclosure, the term "attitude" is meant to be the orientation (either at rest or in motion) of the bird 22 or other object 20 as determined by the relationship between its local Cartesian axes and that of a fixed, global Cartesian axes both of which are shown and discussed in conjunction with FIG. 3. As such, coordinate transformation between the local and global Cartesian coordinates may be used to perform orthogonal transformation between such coordinate systems using known methods, as direction cosine matrices, tensors or other linear vector functions. As discussed elsewhere, some of the acquired data may be fused or otherwise processed in order to make the location determination of the electronic device 100 and the airborne object to which it is attached.

Various forms of location determination may be used, including those based on either angle-measuring approaches or range-measuring approaches. In one form, augmented antenna arrays or related antenna diversity corresponding to angle of arrival (AoA) may be included in, around or on the electronic device 100. In another form, time-of-flight lateration-based approaches such as trilateration (whether time-of-arrival (ToA) as discussed in conjunction with GNSS of extraterrestrial system 40, relative strength signal indication (RSSI)) or multilateration (specifically, time distance of arrival (TDoA)) may be used. Factors such as distance between the electronic device 100 and operations center 200, location where the majority of computational activities takes place, size of the backhaul infrastructure, area of coverage or the like may be used to determine which approach to use. For example, in configurations where the third sub-module 130C of the wireless communication module 130 is transmitting using a LoRa-based signal, long distances between the electronic device 100 (when the bird 22 is at the outer bounds of a coverage area such as a racecourse or other area being monitored) and operations center 200 may make AOA an impractical approach. Likewise, energy-constrained devices such as the electronic device 100 may need to avoid trilateration and its need to perform extensive on-device mathematical computations (including those that may not have closed-form solutions). Moreover, TDoA-based approaches may have limited utility if the bird 22 or other airborne object 20 with the electronic device 100 secured thereto is at the outer bounds of the transmission range. Such may favor other ToF approaches, although relatively straightforward environments (including outdoor environments with clear line-of-sight) may still make TDoA approaches more beneficial than others. When configured using a TDoA approach, the electronic device 100 would act as a signal-generating tag that can signally cooperate with numerous gateways as time-synchronized anchors such that time-stamped location data received thereby can be forwarded to a network server or other portion of computational backhaul. It is understood in such case that the gateway is converting one signal (for example, using a 915 MHz industrial, scientific and medical (ISM) band over an incoming LoRa protocol to an internet protocol (IP) in the backhaul). In one form, one or more gateways may be placed in physical or signal cooperation with the operations center 200.

In one form, the LPWAN is based on a LoRa chipset that employs a chirp spread-spectrum mode of signal modulation. For example, the Semtech® LR1120 family of transceivers (such as the LoRa Edge™ ultra-low power platform that integrates a long-range LoRa® transceiver, multi-constellation GNSS scanner and passive Wi-Fi AP MAC address scanner) may be used to provide multiband LoRa connectivity for terrestrial LPWANs, as well as direct satellite connections such as that needed to communicate with the extraterrestrial system 40. Significantly, using this chipset as a basis for the third sub-module 130C of the wireless communication module 130 enables various form factors, including those small enough to be affixed to bird 22. Moreover, in situations where the chipset that is associated with the third sub-module 130C is configured to perform one or more of the functions of the second sub-module 130B, one of the two sub-modules may be deemed to be subsumed into the other such that functionally both are present, regardless of whether they are part of the same or different underlying hardware components. Relatedly, frequency-shift keying (FSK) and its low-pass filter Gaussian FSK variant (GFSK) may be used instead of LoRa in situations that may have stricter bandwidth (that is to say, noise versus data rate tradeoff) requirements or don't require extremely stringent receiver sensitivity and concomitant reduced robustness against radio-frequency (RF) interference.

In another form, the third sub-module 130C may employ a custom or proprietary communication mode of signal generation and propagation that is built on the same physical layer that exists with a LoRa-based device. In situations where some form of LoRa chipset is used, the devices and systems disclosed herein may utilize various Media Access Control (MAC) or higher layer protocols to ensure the needed wireless connectivity between the electronic device 100 and other parts of the system or equipment cooperative therewith, such as the aforementioned operations center. One such protocol is the LoRaWAN® protocol as a way to establish network connectivity. More particularly, when viewed within the context of an IP suite conceptual model in general and the transmission control protocol (TCP) and the IP in particular, the LoRa chipset defines the physical layer (PHY) while LoRaWAN® defines the MAC layer to define the basic architecture of a LoRa-based network, as well as a procedure for various signal and data transmissions within the network. In this way, the network can leverage inexpensive sensors, beacons and associated components that are situated in nearby data-acquisition devices that are within the communication range of the network in order to aggregate the information contained within these other devices yet take advantage of only requiring the single master device to perform the downstream communication functions. Another protocol may use a combination of technologies (such as some form of FSK along with phase-shift keying (PSK)) that relies on random times and frequencies may be used. On example of such an approach may include Sigfox or other proprietary protocols. Similarities in packet structure, MAC layers and other attributes between some of these protocols may be understood in situations where common goals (such as limiting device power while meeting regulatory requirements for transmission) may be paramount. In one form, it would be possible to run one protocol on another; for example, running LoRaWAN on top of a Sigfox modulation, such as in situations where expanded coverage over disparate LPWAN infrastructures may be operated in the same space. In this way, the electronic device 100 has hybrid IoT-based LPWAN attributes. Details associated with the various forms of wireless communication functionality of the electronic device may be found in aforementioned U.S. Pat. No. 11,147,459, including those associated with two-way modes of communication.

In still another form, the LPWAN is based on a mesh protocol, such as that disclosed in US Published Application 2023/0046739 entitled METHOD AND SYSTEM FOR CONNECTIVITY AND CONTROL OF INDUSTRIAL EQUIPMENT USING A LOW POWER WIDE AREA NETWORK, as well as US Published Application 2023/0084106 entitled METHOD AND SYSTEM FOR CONNECTIVITY AND CONTROL OF A HAZARD-PRONE ENVIRONMENT USING A LOW POWER WIDE AREA NETWORK both of which are owned by the Assignee of the present disclosure and the entirety of which are incorporated herein by reference to the extent that such incorporation does not cause incompatibilities with the present disclosure.

In another form, the LPWAN is based on other protocols or standards, including a HaLow protocol (when used along with an IEEE 802.11ah radio) that can extend the range of more traditional WiFi-based networks, and an NB-IoT standard such as that disclosed in US Published Application 2021/0319894 entitled WEARABLE ELECTRONIC DEVICE AND SYSTEM USING CELLULAR TELECOMMUNICATION PROTOCOLS which is owned by the Assignee of the present disclosure and the entirety of which is incorporated herein by reference to the extent that such incorporation does not cause incompatibilities with the present disclosure.

In another form (and depending on which of the aforementioned factors related to range, energy consumption and bandwidth are needed for a particular data-gathering and signal-propagating mode of system operation), the system may use other LPWAN or non-LPWAN-based protocols, including Wi-Fi, Bluetooth (including Bluetooth Low Energy (BLE), near field communication (NFC), UWB, NB-IoT, LTE-M or lidar, Zigbee or the like. Likewise, communication architectures, including one or both of node-to-node mesh and star topologies, may be used, depending on whether the network need to be self-healing, protocol stacks used or other factors. In addition to receiving and processing wireless signals and communicating data and information, the modes of wireless signal propagation disclosed herein may be used for performing wireless triangulation, lateration or related means for proximity detection. In this way, the communication module 130 may be used for, among other things, exchanging the flight data and the observational data between the electronic device 100 and the operations center 200 over the various communication networks disclosed herein. Depending on the nature of the signal cooperation between the sensors S and the first sub-module 130A, the latter may be equipped to work wirelessly through BLE for use in low data, longer range transmission through a coded physical (PHY) layer, as well as with conventional Bluetooth for use in high bandwidth, shorter distance communications. Likewise, in situations where the sensors S are situated in, or around the electronic device 100 (such as when configured as a SoC or a single-board device), signal conveyance may be through a wired connection. It will be appreciated that either configuration is within the scope of the present disclosure.

In one form, the sensors S that are on other devices that are within communication range of the network, as well as on-body sensors of the wearer, could send data to the master device for subsequent conveyance to the larger network. In this way, the network as disclosed herein may be used in conjunction with an individual or group of individuals to communicate and exchange data that in turn may be analyzed for determination of one or characteristics of the person or people associated with the device or devices 100. Within the present disclosure, the exchange of information (such as flight data and the observational data) across the network and portions thereof (such as between the electronic device 100 and the operations center 200) are understood to include one or both of unidirectional and bidirectional attributes.

As previously noted, in one form the IMU $S_1$ can provide dead reckoning information. For example, position information may be derived from the accelerometer data by two successive integrations. Typically, such a calculation leads to drift errors. In one form, the dead reckoning position data from the IMU $S_1$ is coupled to the satellite-based guidance and locationing data of the extraterrestrial system 30. Such a combination helps to provide an increased degree of signal continuity even when subsequent to the combination the GNSS signals are blocked for a period of time (such as when the object being detected is in a tunnel, inside a building, under thick foliage or the like). In one form a sensor fusion algorithm used for the INS, GNSS or other modes of individual location determination may be based on a Kalman filter to integrate the IMU $S_1$ and other sensor S data that is continuously available with the potentially-intermittent yet accurate extraterrestrial system 40 or terrestrial system 30 data in order to make an aggregate location determination. Moreover, when using the ML functionality disclosed herein, the Kalman filter may be used as a basic part of a Bayesian network or other time series (or related recursive) forecasting, such as gradient boosting, neural network, especially for acquired data with extensive temporal or dynamic components as long as the data used to train the model is older than the validation data.

When configured as an INS, computer-based algorithms and additional sensors S may also be used to ascertain dead reckoning and related information in an attempt to form a more complete understanding of the object's position, orientation and velocity. In one form, the sensors S may be separate components distributed on or around the bird 22 or other object being monitored as part of a distributed sensor network in order to acquire location, orientation, physiological, environmental, activity or other related data, while in others as part of a singular package in a manner similar to that used in the IMU $S_1$.

As previously noted in conjunction with FIG. 1, the data (such as that acquired through the sensors S) that is received by or otherwise input into the operations center 200 may be stored, processed and analyzed locally on the electronic device 100, the base station 210, the portable device 220, the cloud 230 or servers 240. In one form, the electronic device 100 possesses the capability to seamlessly connect and communicate with external networks (not shown) that encompass systems, components or the like with these or other forms of distributed computational functionality. Such external networks may include local area networks (LANs), virtual private networks (VPNs), server farms, computer clusters or the like. As with the cloud 230, some of these networks may be constructed as numerous interconnected nodes each of which is capable of performing distinct capabilities, including autonomously executing any or all of the functionalities elaborated in this disclosure. The versatility of these nodes is underscored by their potential configurations, whether as handheld devices (including mobile telephones or personal digital assistants as exemplified by the portable device 220 and which may be configured as a tablet, smartphone, portable computer or related mobile platform), laptop systems, SoC, multiprocessor system, thick or thin client-based devices, personal computing devices, expansive networks ranging from minicomputers to mainframe systems, or even as part of a decentralized computing architecture that assimilates any or all of the devices or systems previously mentioned. In the illustrative extension depicted in FIG. 1, the server 240 of may be configured as one such node within this networked ecosystem, as are the various components depicted in the operations center 200. Relatedly, certain network protocols may be implemented for the cloud 230 depending on the degree of statelessness (for example, the IP or HTTP variants) or statefulness (or stateliness, in either event such as the TCP, FTP variants).

In this form, the cloud 230 can provide content, analysis, network access and related services in a shared, real-time or on-demand manner to various configurable computing resources. The use of the cloud 230 may encompass various characteristics, service-providing models and modes of deployment. For example, characteristics of cloud 230 may include on-demand service, broad network access (such as through any of the aforementioned nodes), the ability to pool resources (including dynamically-assignable variants) using a multi-tenant model, rapid scalability and measured service (to provide processing, bandwidth, storage or related metering capability). Likewise, services that can be provided by cloud 230 include (depending on an end-user's desired degree of involvement in how such service is created, configured or managed) either software as a service (SaaS), platform as a service (PaaS) or infrastructure as a service (IaaS). Furthermore, modes of deployment of cloud 230 may include (depending on an end-user's desired autonomy as well as associated security or access control concerns) a private cloud, a community cloud, a public cloud or a hybrid cloud.

Figure 3:
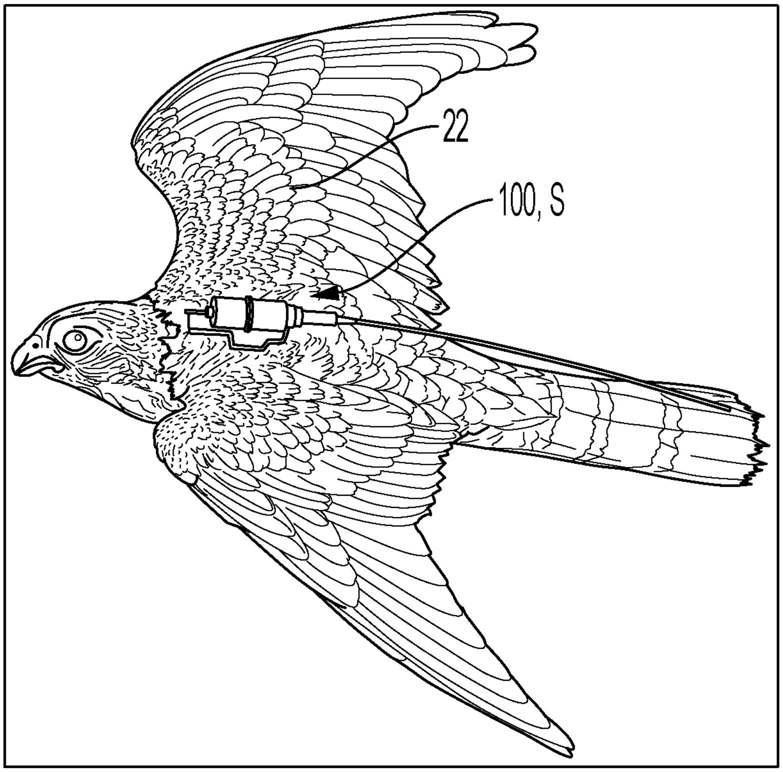
FIG. 3 depicts a notional attachment of the electronic device to a bird of prey.

Referring next to FIG. 3, one embodiment the placement of the electronic device 100 onto a bird 22 is shown. Although presently shown being affixed in a backpack-like manner, it will be appreciated that other means of affixing, including different form factors or mounting locations, are envisioned all of which are within the scope of the present disclosure. In one non-limiting form, the electronic device 100 (as well as any packaging needed to satisfy the intended form factor) could take the shape of a lightweight anklet, collar, harness or other relatively unobtrusive size and shape, including those that distribute the weight of the components or assembled whole evenly across the body of the bird 22. In one form that may be appropriate for larger birds, a more robust package design (potentially embedded within wing tags or the like) could be employed. Likewise, for smaller birds and related animate objects beings like insects, the device could be miniaturized to fit as a tiny backpack. Although not shown, in one embodiment the electronic device 100 may be small enough to allow it to be woven into feathers, thereby acting as a nearly invisible sentinel for use in monitoring health, environment or other desired parameters in real-time. Significantly, ergonomics, material choice, weight distribution and related concerns help ensure that the electronic device 100 does not hinder the natural behavior and flight patterns of the bird 22 or other species being monitored.

Figure 4:
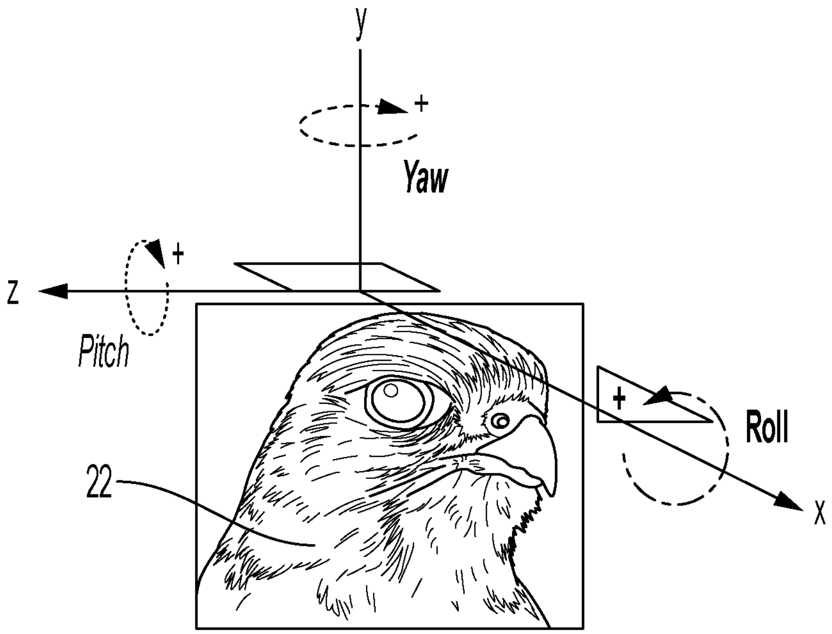
FIG. 4 depicts the Cartesian coordinate system that forms a reference point for the degrees of freedom of movement of the bird of prey of FIG. 3.

Referring next to FIG. 4, the major axes of a Cartesian system and the 6-DOF of movement of the bird 22 is shown. In particular, each of the three axes (that is to say, x-axis, y-axis and z-axis) defines one degree of freedom of translational movement and one degree of rotational movement. Within the present disclosure, the translational degrees of freedom of movement are as follows. The x-axis coincides with a longitudinal forward or backward view when the bird 22 is engaged in straight, level flight. The y-axis coincides with a vertically upward or downward view when the bird 22 is engaged in straight, level flight. The z-axis coincides with a lateral (that is to say, left or right) view when the bird 22 is engaged in straight, level flight. The corresponding rotational degrees of freedom of movement are the roll, yaw and pitch axes, respectively. These axes and their respective degrees of freedom are beneficial in understanding the movement of the bird 22 that is picked up by one or more sensors, as well as how such movement fits into a larger flight path or pattern that can be mapped or otherwise visualized. These degrees of freedom of movement of the bird 22 may be sensed by either a 6-DOF or a 9-DOF version of the IMU $S_1$ as previously discussed. In one form, one or more of the environmental sensors $S_2$ and physiological sensors $S_3$ may be placed at different locations on the bird 22 and made cooperative with an optical measuring system such that they act like fiducial markers. In one form, such an approach may be used for location mapping, moving map displays or the like. In this way, real-time tracking and analysis of the movement, behavior and environmental interactions of the bird 22 may be better understood.

As previously noted in conjunction with FIGS. 1 and 2, a sensor fusion algorithm (also referred to herein as a fusion engine) may be used to combine (in addition to other acquired data) the accelerometer, gyroscope and magnetometer data of IMU $S_1$ into stable Cartesian space orientation. This is especially valuable when the airborne object is the bird 22, which often makes rapid capitulations, head movements or the like. It will be appreciated that the sensor fusion algorithm may perform other types of data source anonymization, such as that which is being acquired from any of the other forms of sensors S, including the ones that form part of the electronic device 100. Moreover, in situations where one or more of the devices within the bird training and optimization system 1 are functioning as IoT-based equipment, the data being acquired may be put into universally-available form through the aforementioned semantic layer or other form of preprocessing, cleansing or related manipulation. In one form, the microcontroller 110 may be configured (through its processor 110A, memory 110B and program code 110E) to perform any necessary sensor fusing algorithms on its own, while in another the electronic device 100 may include additional specialized processors such as an ARM Cortex-M0 family of processors (that itself may act as—or in cooperation with—the microcontroller 110, including as a SoC) to collect the data from the sensors S and abstract away the sensor fusion and real-time requirements such that the resulting data may be used in use in quaternions, Euler angles, vectors or the like. In one form, the inclusion of sensor S fusion in conjunction with the controller 110 provides the bird training and optimization system 1 with hardware-agnostic recognition of the bird 22 and its various movements and related activities in order to arrive at improved information related to heading, Cartesian axis pitch, yaw and roll, linear acceleration and gravity, such as that available from a 9-DOF IMU $S_1$. In one form, the memory 110B can store a mapping module that includes program code 110E that when executed by the processor 110A cause the processor 110A to extract one or more features from one or more data sets (including those involving baseline data as well as those involving present, real-time data). Within the present context, various forms of mapping may be achieved, including mapping for features related to local terrains or environments, as well as mapping for features related to the type of data, the source of data, how the data is formatted within such source or the like. In this way, various services related to device software, data and control may be implemented in the electronic device 100 in order to allow it and other devices that are cooperative therewith to operate in a more universal (that is to say, agnostic) manner, regardless of particular hardware or software configurations. In one form, this can promote data management for the purpose of conducting edge computing operations, especially as it relates to certain amounts of data preprocessing, such as to reduce the burden on memory, connectivity or bandwidths associated with the various nodes that make up the communication to and from the electronic device 100.

In one form, any fusion of sensor data and an associated algorithm may further improve location-measuring accuracy for both absolute distance as well as update speeds with very little latency. Within the present disclosure, the fusion of sensor data may result from using numerous tracking or location approaches. By way of example, the fusion may combine the inertial data (such as that taken from the IMU $S_1$) and visual, optical or RF tracking means (including those from the extraterrestrial and terrestrial systems 30, 40). One such motivation to combine these two forms relates to using the IMU $S_1$ for tracking rapid movements, while the optical sensors (and their ability to provide absolute reference points) may be used to compensate for integration-based introduction of drift or related errors, as well as misalignment and other errors. In one form, feedback-based approaches may be used when environmental and related changes occur. In this form, one or more algorithms may be used to review and make judgments on the acquired data, especially in time series events such as disclosed herein. This in turn permits the dynamic switching of how the sensor fusion and associated algorithms are performed. In one form, such a dynamic approach may be used for intent sensing or other predictive algorithms, such as through the aforementioned Bayesian fusion of the sensors S data where the training of the ML model 800 may take advantage of individual sensors S whose role is susceptible to dynamic updates.

As previously noted, pose tracking may be used to detect the precise pose of head-mounted displays (such as those used in AR and VR), controllers, other objects or body parts within Euclidean space. Pose tracking is often referred to as 6-DOF tracking for the ways in which the pose is often tracked. Although having some similarities to positional tracking, pose tracking further includes orientation that positional tracking does not. As noted elsewhere, magnetometers and other IMU $S_1$ equipment may provide partial orientation information, although not the full orientation that pose tracking provides. It will be appreciated that any of the forms and combination of data sensing as disclosed herein may be used to acquire precise measures of orientation, position and related data. In one form, the fusing of this form (as well as other forms) of received data may take place through the aforementioned Kalman filtering (including extended or invariant versions thereof), as well as other forms of filtering such as weighted averaging, maximum likelihood, sequential Monte Carlo filtering, Hidden Markov Models, Bayesian estimation algorithms, other state space models or the like. In one form, the various forms of acquired data from the sensors S may be fused in order to produce a Cartesian-based form of the pose tracking for the bird 22. Furthermore, such information may be processed for other uses, such as visualization or the like that may be displayed on one or more of the components or resources depicted in FIG. 1. In one form, the results sensor fusion may be used to establish position of the bird 22 as it moves through the race-course, training ground or other space of interest. In such case, additional data in the form of known reference positions (such as those known from landmarks, terrain mapping, GNSS-derived data or the like), may be combined with recent or other forms of historical movement data (included that generated by the ML model 800 that is run on the electronic device 100) in order to track the path of the bird 22.

It will be appreciated that the collection of large quantities of inertial, geoposition and physiological data that are associated with the bird 22 and its movement is going to require significant amounts of computing power with which to provide meaningful analysis. One way to glean such meaning is by including machine code 110E that can facilitate a sensor fusion algorithm. Thus in one form, the sensors S used to gather GNSS geoposition data from the extraterrestrial system 30, inertial information from the IMU $S_1$ and the physiological sensors $S_3$ may be fused using time series-based forecasting and related statistical methods for both the spatial and temporal data. In another form, the fusing of data from the same one of sensors S may be done as part of a regression-based analysis. As will be discussed in more detail as follows for either type of fusing, some of these time series methods are based on the aforementioned Kalman filtering, as well as on such filtering in conjunction with Bayesian and neural networks the last of which is particularly in the form of the aforementioned CNNs or RNNs the last of which is beneficial in considering historical and prior event data. In one form, the RNN may form an LSTM network where the LSTM units may be trained over a series of temporal (i.e., time-based) sequences such as those associated with the data that is being acquired by the IMU $S_1$. In one form, gradient descent in addition to backpropagation may be used as an optimization algorithm to augment approaches such as hidden Markov) that may be sensitive to vanishing gradients for certain training data configurations, ensuring that the model remains robust and adaptable across a diverse range of flight patterns and physiological indicators. In situations where the prediction of future elements of a given temporal sequence based at least in part on historical information is involved, LSTMs are particularly useful, especially in situations where information associated with multiple input variables such as those of the sensors S and the geoposition data is being acquired, particularly where the amount of data being acquired is voluminous.

Figure 5A:
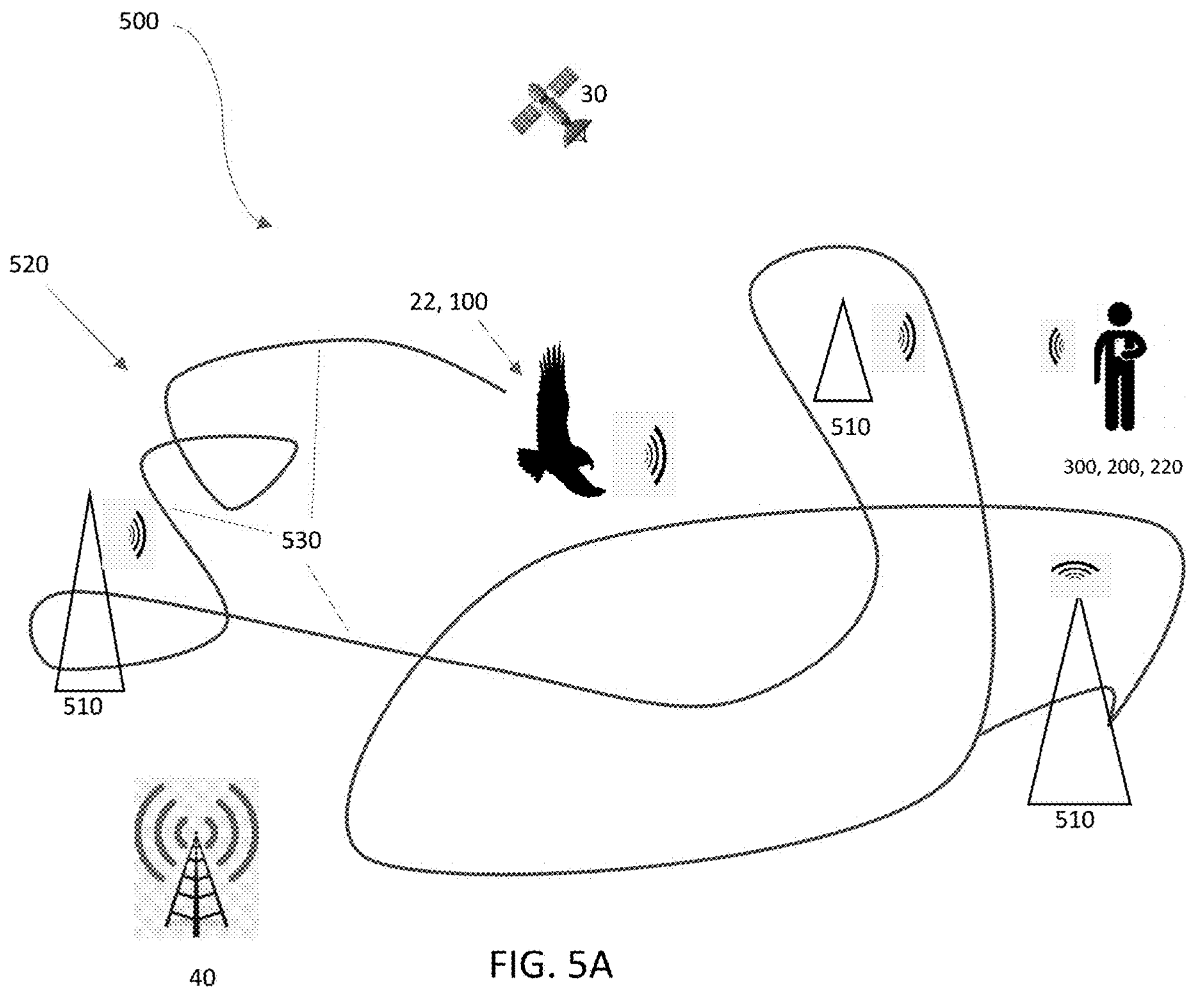
FIG. 5A depicts a notional flight pattern of the bird of FIG. 1 on a course.
Figure 5B:
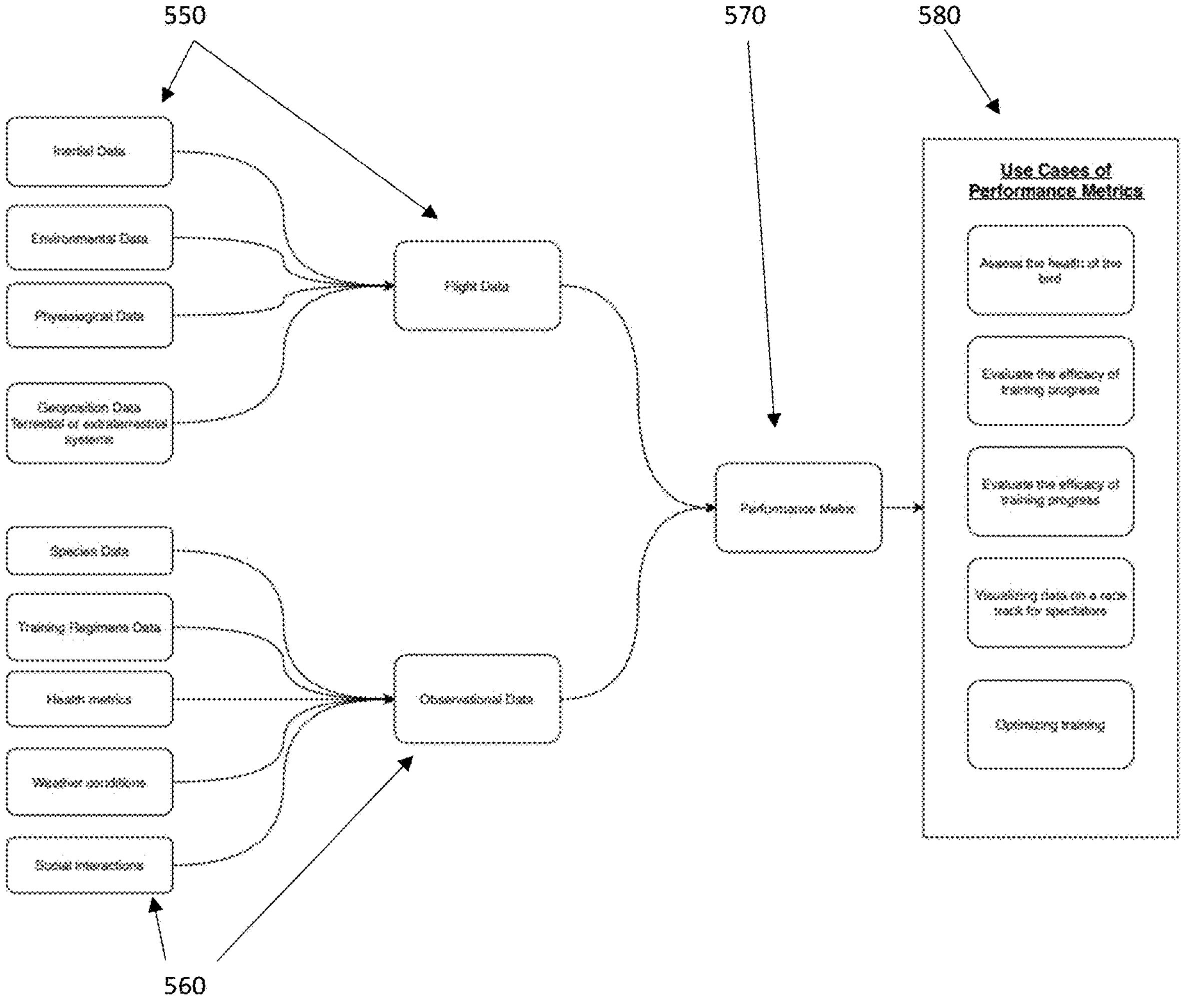
FIG. 5B depicts how flight data and observational data acquired from a bird on the course of FIG. 5A flows into a performance metric along with possible use cases.

Referring next to FIGS. 5A and 5B, a course 500, such as that demarcated by numerous navigation beacons 510 (shown in the form of cones or towers)—along with how data acquired while the bird 22 is traversing part or all of the course 500 is used for the purpose of determining performance metrics for possible use cases—is shown. As previously noted, the electronic device 100—either autonomously as an edge device or in conjunctions with the operations center 200 or other backhaul—processes the data acquired by the sensors S, extraterrestrial system 30 and (optionally) the terrestrial system 40 in order to analyze the flight data 550 that corresponds to the bird 22 while it is traversing the course 500. One or more forms of observational data 560 as previously discussed may also be detected. As noted elsewhere, some forms of the observational data 560 may be acquired through other means (such as that readily ascertainable by the individual 300, known baselines such as weather forecasts or readings, prior regimens or other forms), while other forms may be acquired through one or more of the sensors S (including those that form part of the electronic device 100) or other sources. Together, the flight data 550 and the observational data 560 may be combined or otherwise utilized (such as by the ML model 800) to arrive at one or more performance metrics 570 and one or more use cases 580. Within the present disclosure, the term "flight data" includes both data related to one or a small number of individual metrics (for example, speed, heart rate, local environmental condition, lap time around the course 500 or the like), as well as in the aggregate as acquired from most or all of the sensors S and extraterrestrial and terrestrial systems 30, 40. Thus in one form, the flight data 550 may include any or all data needed to provide an objective measure of the performance of the bird 22, whether it is for a time around the course 500 (such as in a sporting competition, training, diagnostics or the like) or its overall health (such as that measured by the various environmental and physiological sensors $S_2$, $S_3$, possibly in conjunction with its speed and location information as acquired by the IMU $S_1$ and extraterrestrial system 30). Within the present disclosure, the term "performance metric" includes any qualitative or quantitative measure that provides insights into the bird's abilities, health, or responses to stimuli under different conditions. Performance metrics 570 may encompass both inherent qualities of the bird 22 in its natural state, as well as qualities that can be influenced or trained. Such metrics range from specific physiological markers indicating the bird's state of health or stress to behavioral indicators that may shed light on its agility, alertness or responsiveness. Metrics may also capture interactions between the bird 22 and its environment, gauging its adaptability or resilience under changing conditions.

Performance metrics 570 are flexible depending on the needs of a particular stakeholder (such as a trainer, biologist, owner or the like), and may encompass one or more different types in order to assess and support the wellbeing and capabilities of the bird 22. As such, the performance metrics 570 that are generated based on the processing of the various forms of received data may be analyzed directly, as well as against certain references, baselines, norms or benchmarks. Moreover, in situations where the performance metric 570 is correlated to a condition of interest (for example, a health condition of the bird 22), when such metric falls outside an acceptable threshold, quantity or other value, the electronic device 100 can generate an alert (visual, audible, haptic or the like) that can be conveyed to the individual 300 or other interested parties. Thus, the acquired flight and observational data 550, 560 (either in combination or individually) may be used to monitor and detect physical and behavioral signs (such as the aforementioned biomarkers, regardless of whether they are quantitative or qualitative) of the bird 22 to track changes in its physical and cognitive health. In one form, such alert may be conveyed wirelessly using the third sub-module 130C to a suitably-equipped receiver, as well as be stored in memory or displayed on the electronic device 100 the latter of which through the aforementioned GUI or other component. In addition, one form of output from the inference engine produced by the ML model 800 may include suggestions on how to alter a training regimen or the like. With particular regard to comparison of the metrics against such reference, clear, quantifiable indicia of whether the bird 22 is performing better or worse as a result of a certain training regimen, diet, age, environment or other factor. Regardless of whether the performance metrics 570 are analyzed in the abstract or against a reference, the operation of the system in general and the electronic device 100 in particular facilitates real-time or near real-time insights, including the conveyance of such insights into one or more of the stakeholders or other individuals that have an interest in the health or other aspects of the bird 22.

Relatedly, the performance metrics 570 can be measured in the performance or physical attributes of the bird 22. Examples of such performance-related metrics may include (i) the time to complete a predefined task, (ii) precision or accuracy in the performance of a particular task, (iii) maneuverability or agility and (iv) repeatability, reliability or confidence level in one or more of the foregoing. Examples of such physical-related attributes may include (i) speed (which is indicative of the health and energy levels of the bird 22), (ii) stamina (which is indicative of the ability of the bird 22 to perform and recover quickly after a long flight or difficult hunt, race or other competition), (iii) endurance (which is indicative of the ability of the bird 22 to maintain consistent effort over extended durations), (iv) strength (which is indicative of the physical power of the bird 22) and (v) coordination (which is indicative of the ability of the bird 22 to harmoniously align its movements and reactions). In one form, any significant change in one or more of these five physical attributes may serve as early warning signs which may be indicative of the onset of stress, health issues, environmental changes, or other conditions. As such, these early warning signs may be used as part of a predictive analytics determination and reporting based on the ML processes discussed herein, whether taking place at the edge or in some other part of the bird training and optimization system 1.

In addition to the flight data 550, the electronic device 100 may be used to acquire information about the course 500 itself. In such case, the navigation beacons 510 may actively send their individual position. This in turn can be mapped by the electronic device 100 or operations center 200. Significantly, the navigation beacons 510 may actively send position updates of the bird 22 as it passes nearby. In one form, detection of the presence of the bird 22 may be made using radio frequency ID (RFID), lidar, radar, acoustic, visual (including cameras) or other related equipment; this in turn is conveyed to the electronic device 100.

In one form, one or both of the performance metrics 570 related to the bird 22 and the mapping of a flight path 520 (or individual maneuvers 530 thereof) may be placed onto a display or related visualization device such as that associated with the aforementioned portable device 220 for use by the individual 300; such metrics may also or alternatively be placed onto a data file, hardcopy printout or the like. In one form, the performance metrics 570 may be the culmination of all of the data that has been acquired by the sensors S, extraterrestrial system 30 (and optionally from one or both of the terrestrial system 40 and observational data 560 from the individual 300) during a particular diagnostic, training, racing, hunting or related activity of the bird 22 either in flight or pre- or post-flight. In a related manner, the electronic device 100 operates to fuse the acquired geoposition, inertial, environmental and physiological data into flight data 550 of the airborne bird 22. In one form, such fusion may include one or more of the gathering or receipt of the raw data, preprocessing or related cleansing of the data, as well as storage of the data. For example, the storage may be for one or multiple instances of transmission such that if real-time transmission is not always possible, a portion of the program code 110E may allow for the storage in memory 110B (if on-device) or remote memory (for example, that connected to the cloud 230, servers 240 or other backhaul-based computer-readable medium) of numerous instances of time-stamped data that could be later sent, such as when a transmission or remote receipt window becomes available. In one form, program code 110E may first make a determination as to whether a delay in receipt of the data involves an acceptable or unacceptable degree of loss of data integrity such that if the former, it can instruct the communication module 130 (in general) and the third sub-module 130C (in particular) to transmit the data to the operations center 200, individual 300 or other location where actionable intelligence related to the data may be needed. The preprocessing of the data (whether being done for general cases where dimensionality reduction, normalization, correction of data sparseness or other pre-analytical operations are being conducted, as well as for part of training the ML model 800 or performing inferences with it) is often necessary to clean the data and convert it into a form from which condition indicators may be extracted. Within the present context, such data preprocessing may include one or more of outlier and missing-value removal, offset removal, detrending, noise reduction (such as filtering or smoothing) and transformations between time and frequency domain (such as through advanced signal processing using short-time Fourier transforms and transformations to the order domain).

In one form, the course 500 is used for training of the bird 22, while in others as a sporting venue such as a race course, simulated hunting ground, actual hunting ground or the like. By using the navigation features provided by the electronic device 100 or other part of the bird training and optimization system 1, the various individual maneuvers 530 that in the aggregate define the fight path 520 may be understood. Such understanding aids in determining the proficiency of the bird 22 in completing its task in an efficient and effective manner. As shown, the navigation beacons 510 are actively sending position and detection data (including RFID, lidar, radar, acoustic, visual or the like) to one or more of the electronic device 100, operations center 200, individual 300, extraterrestrial system 30, terrestrial system 40 or to one another using known forms of RF signals. These signals facilitate real-time monitoring, ensuring a seamless feedback loop and visualization for trainers, spectators or handlers or other interested individuals.

As previously noted in conjunction with FIG. 2, the first sub-module 130A is used to receive, collect or otherwise acquire data from the sensors S, while the second sub-module 130B is used to receive, collect or otherwise acquire data from the ground or sky through the terrestrial system 40 and extraterrestrial system 30, respectively. In one form, Kalman filtering data plus IMU $S_1$ data may be used in order to achieve this visual, camera or related image-based estimate of one or more of position, velocity, orientation and other components related to bird 22 navigation. In one form, different modes of tracking may be employed over different parts of the course 500. Thus, for example, during certain portions of the flight path 520, inertial data may be used for position determination, while for other portions, visual, radio frequency or other acquired data may be used. In one non-limiting form, different parts of the course 500 may correspond to the regions between each of the navigation beacons 510 or other cones, towers, air gates or the like. In other parts of the flight path 520, data from one or both of the extraterrestrial system 30 and the terrestrial system 40 may be used. As discussed elsewhere, some or all of these forms of data may be fused in order to derive an accurate understanding of the position, speed or other parameter of interest of the bird 22. In one form, information from high speed timing equipment such as that used in conjunction with the navigation beacons 510 may be used for additional fusing and further increase in the accuracy of position and velocity measurements, such as is used in racing.

In one form, the training regimen may be performed using the course 500 or other known venue, location or region of interest (such as a falconry park). Regardless of the venue, the training regimen may include one or more of a combination of exercises, conditioning activities and skill-building tasks designed to improve the flight capabilities of the bird 22, physical fitness, navigational abilities, or adaptability to various environmental conditions. The training regimen may be tailored to the specific needs or characteristics of the bird 22, taking into consideration factors such as age, species, health status, natural behaviors or any other relevant attributes. In one form, the training regimen may be tailored for other purposes, such as the bird 22 police a vineyards or other place of interest where it is valuable to deter small animals, rodents, other birds or other pests from entering into the place of interest. Likewise, the training regimen may include, but is not limited to, exercises and conditioning activities designed to enhance the aerial agility, speed and stamina of the bird 22. Furthermore, the regimen may incorporate skill-building tasks focused on improving the ability of the bird 22 to achieve these objectives, such as to effectively detect, target and deter those animals, birds, pests or the like that pose a threat to the place of interest. The training regimen may also involve familiarization with the specific environment associated with the location of interest, including its topography or other layout specifics, common animal threats, and any relevant sensory cues or signals. In addition, the training regimen may take into consideration the age, health status or other relevant attributes of the bird 22 to ensure optimal effectiveness in safeguarding the vineyard, garden, orchard or other place of interest. In situations such as this, it will be appreciated that the bird 22 may include the aforementioned falcon, as well as owls (such as barn owls), bluebirds, hawks or other birds that can be trained to protect crops from ground-based or airborne pests.

Building on the aforementioned training approaches, several methods can be employed to train and acclimate the bird 22 to specific tasks. Techniques may include lure (also referred to as telwah) training, which is similar to creance tethering where the bird 22 is attached to a line to ensure it doesn't fly away during the initial training phases. Another technique includes balloon-based training where meat or other enticing items are attached to a helium balloon to stimulate predatory behaviors and aerial dexterity in the bird 22. Additionally, the use of drones or aircraft for training may be used to simulate flight patterns, mimic prey movement or create specific aerial challenges for the bird 22.

In one form, the process begins with the bird 22 undertaking a designated task. The bird training and optimization system 1 then evaluates the performance of the bird 22 against a set benchmark or desired outcome. Based on this assessment, the performance is scored or evaluated, paving the way for the bird training and optimization system 1 to formulate a comprehensive training regimen. This regimen considers various facets, including physical, emotional, social and environmental parameters, in order to refine and enhance the performance for future tasks.

This systematic approach provides granular insight into the capabilities of the bird 22, including strengths as well as areas needing improvement. The tailored regimen may further envelop a combination of exercises, conditioning routines and skill-enhancement tasks that cater specifically to the unique needs or attributes of the bird 22. For instance, if the goal is to employ the bird 22 to patrol and safeguard specific locations such as vineyards from pests, the training regimen would be structured to improve its aerial agility, detection abilities and targeting precision. This holistic training approach not only encompasses physical drills but also familiarizes the bird with specific environmental cues of the location, common threats and other matters of particular importance to the location for which the bird 22 is being trained. Furthermore, such an approach equips the bird 22 with strategies to effectively counter known or specifically-identified challenges. Such adaptability in the regimen ensures that regardless of the age, health or other attributes of the bird 22, it remains competent and efficient in its designated role, whether in a vineyard, garden, orchard or any other place of interest. It will be appreciated that other locations and uses for the bird 22 are envisioned, and that all such uses and locations are within the scope of the present disclosure.

Figure 6A:
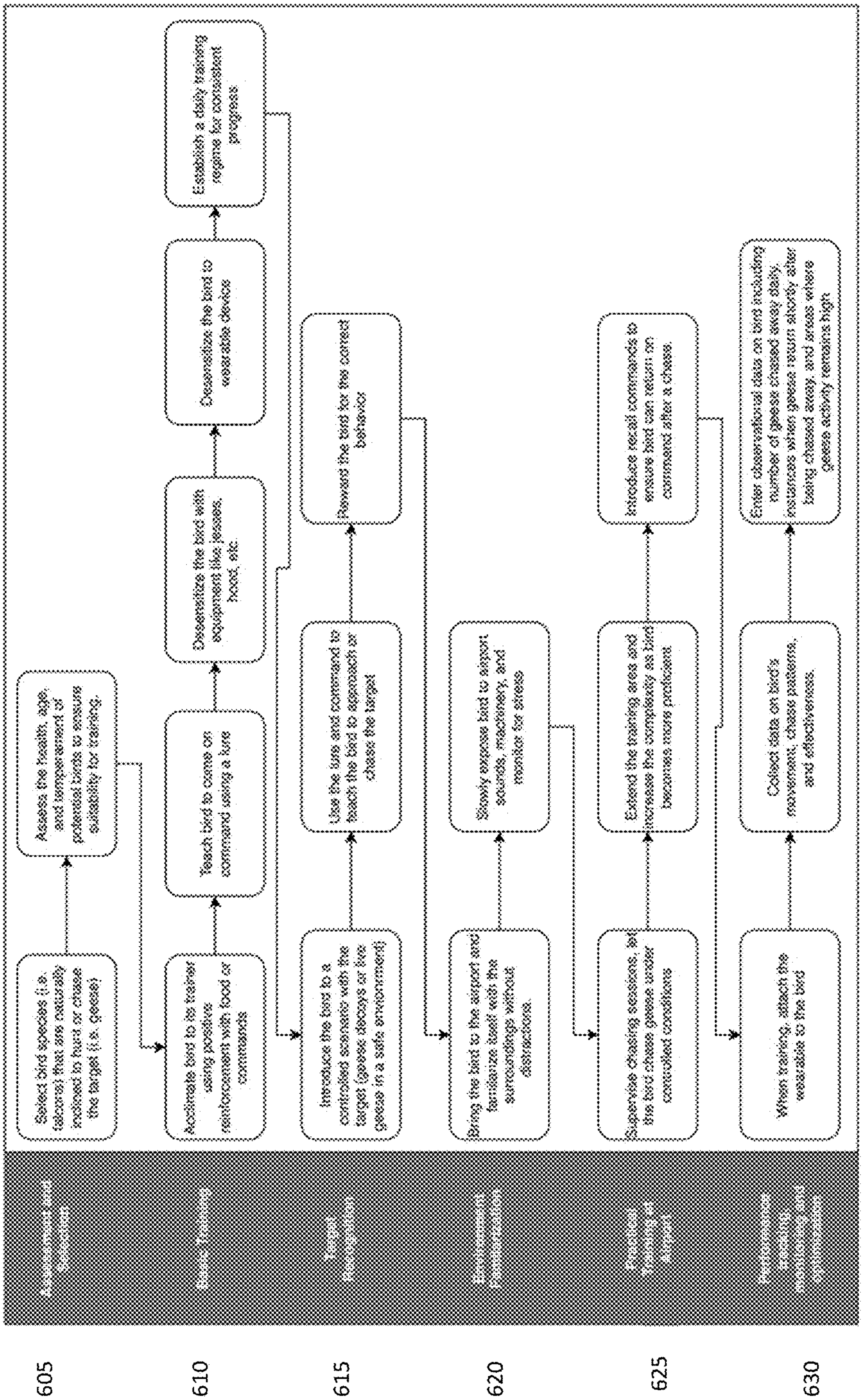
FIG. 6A—depicts a program structure in the form of a flow diagram of how the electronic device may be used to train, a bird to chase away geese from an airport.
Figure 6B:
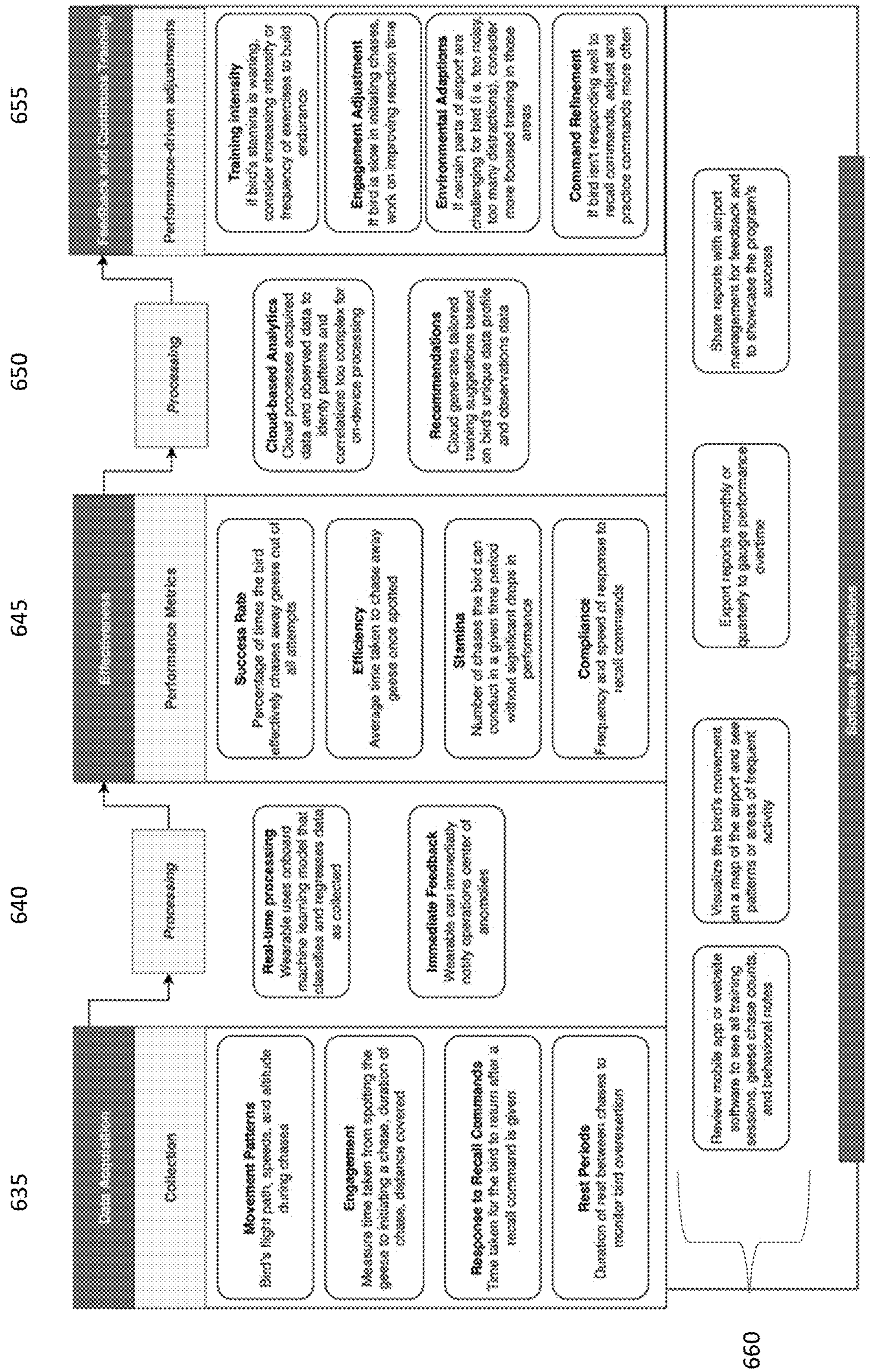
FIG. 6B depicts a program structure in the form of a flow diagram of how the data acquired by the electronic device is subjected to various forms of processing, as well as how performance metrics of a falcon being trained under the regimen of FIG. 6A may be updated.

Referring next to FIGS. 6A and 6B, one example for training the bird 22 is now described. It is beneficial in areas in and around commercial airports to safeguard aircraft during takeoff and landing against others birds such as geese that often congregate. As shown, a regimen is established to train the bird 22 to chase away these and other nuisances in order to safeguard such airports.

Referring with particularity to FIG. 6A, in a first step 605 (assessment and selection), the bird 22 is selected and assessed for various metrics. In a second step 610 (basic training), the bird 22 is acclimated to its trainer (which in one form is embodied as individual 300 in FIG. 1), after which the bird 22 is taught to follow lure-based commands, be desensitized and establish a daily training regime. In a third step 615 (target recognition), the bird 22 is introduced into a controlled scenario where the lure is used and rewards earned. In a fourth step 620 (environment familiarization), the bird 22 is brought to a particular airport in order to become familiar with it and the sights, sounds and other possible sources of stress. In a fifth step 625 (practical training at the airport), the bird 22 undergoes supervised training sessions so that as the bird 22 becomes more proficient, the training area may be extended, as well as be exposed to recall commands. In a sixth step 630 (performance tracking, monitoring and optimization), the electronic device 100 is secured to the bird 22 in order to collect various forms of data, while observational data 560 (such as that related to the ongoing presence of geese in one or more particular areas of the airport) is also entered, such as to one or both of the electronic device 100 and operations center 200 over one or more communication networks as described herein. As described elsewhere herein, the performance metrics 570 may in one form be determined by combining the flight data 550 and observational data 560, such as through the edge-based ML functionality of the electronic device 100, or from other locations such as the operations center 200.

Referring with particularity to FIG. 6B, the data that was acquired by the electronic device 100 during a data acquisition step 635 may be subjected to a first processing step 640 to determine under, an effectiveness step 645, how performance metrics 570 of FIG. 5B of the bird 22 that was trained under the regimen of FIG. 6A may be updated. This output is then subjected to a second processing step 650 so that under a feedback and continuous training step 655 adjustments to the training regimen the bird 22 may be effected. In step 660, various forms of software-implemented ways of conveying one or more of data, diagnostics and predictive analytics to the individual 300 or other interested party (such as through various communication protocols discussed herein).

Figure 7A:
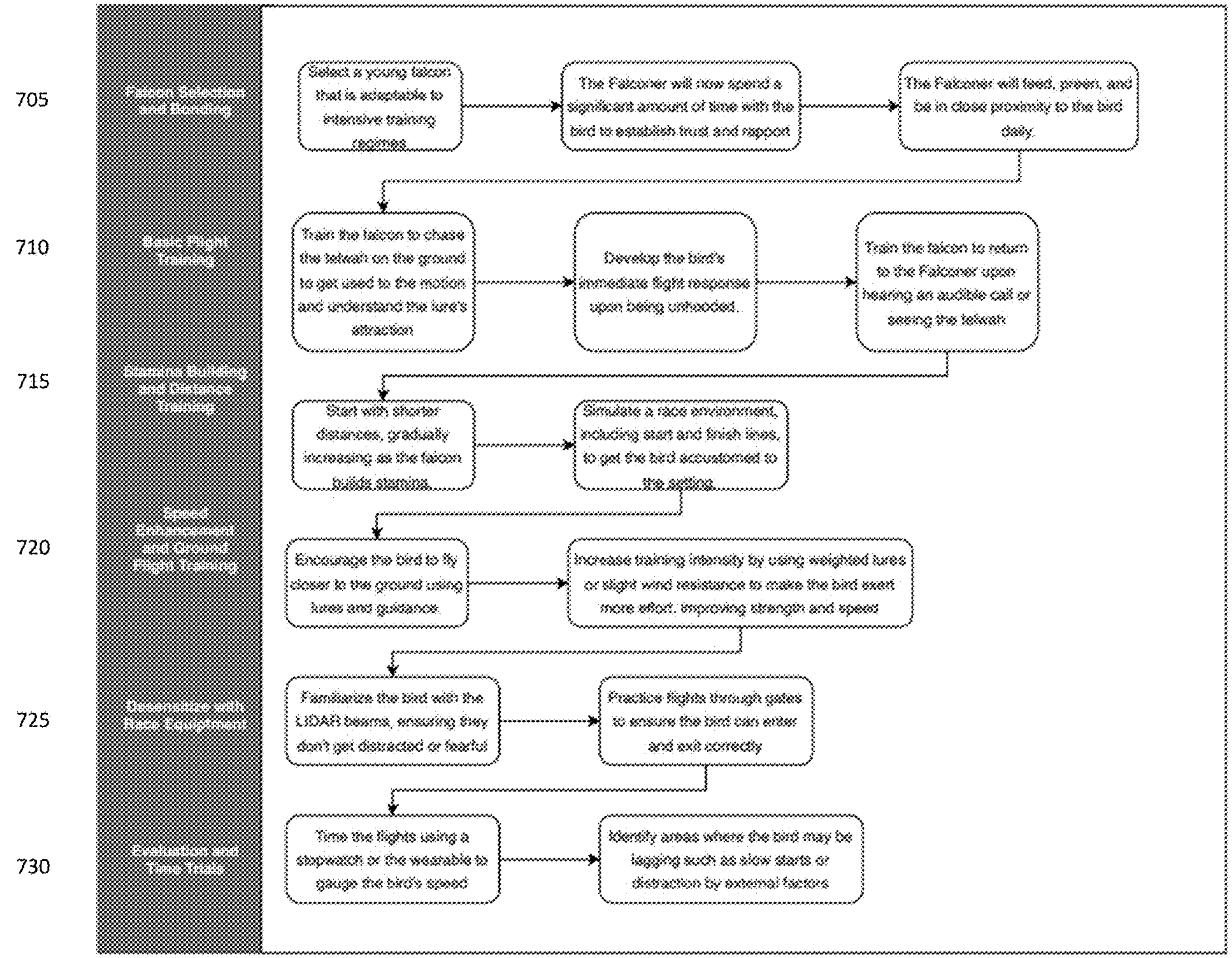
FIG. 7A—depicts a program structure in the form of a flow diagram of how the electronic device may be used to train, track and evaluate falcon telwah performance.
Figure 7B:
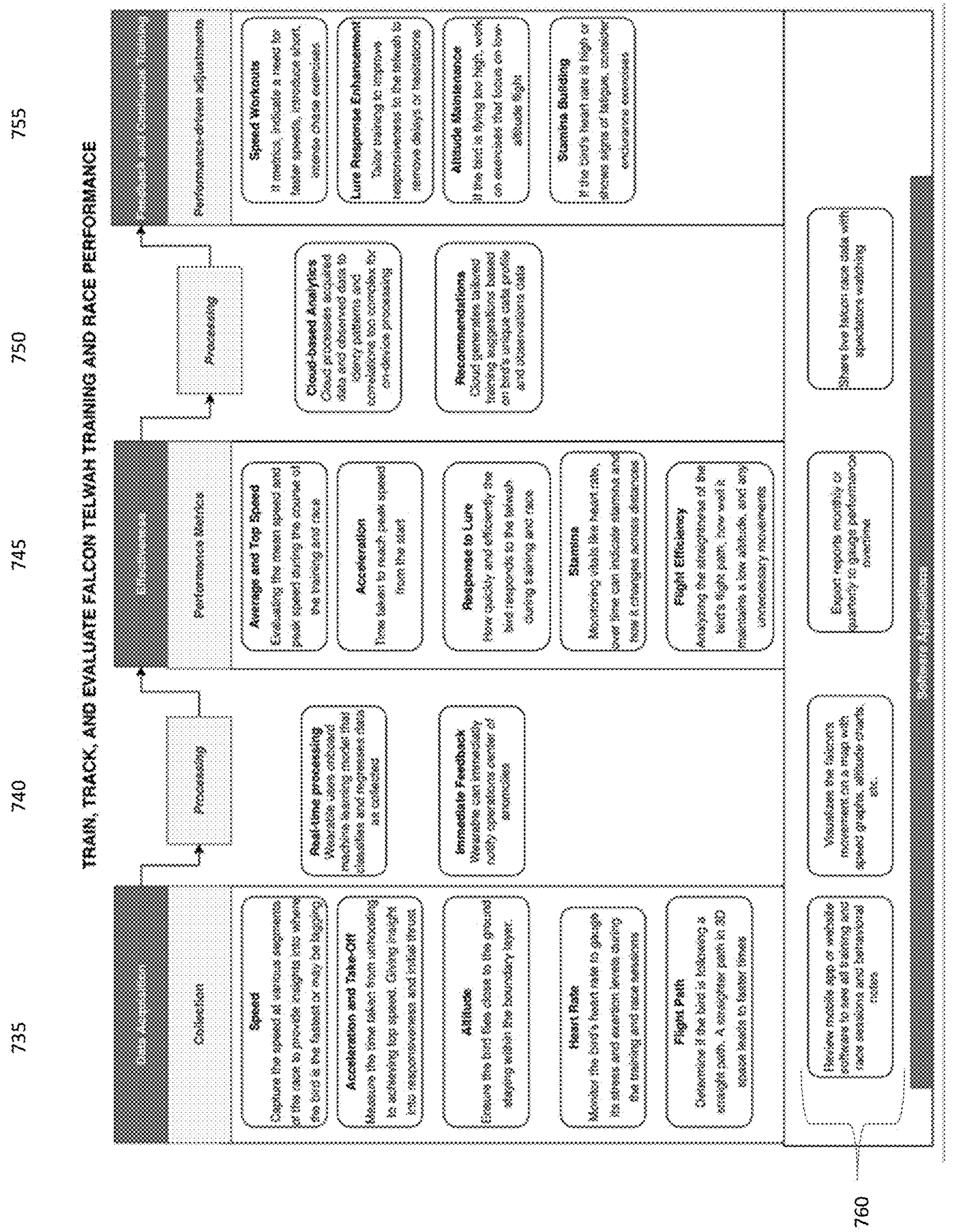
FIG. 7B depicts a program structure in the form of a flow diagram of how the data acquired by the electronic device is subjected to various forms of processing, as well as how performance metrics of a falcon being trained under the regimen of FIG. 7A may be updated.

Referring next to FIGS. 7A and 7B, another example for training the bird 22 for a different mission than that described in conjunction with FIGS. 6A and 6B is now described. In particular, telwah training may be performed on the bird 22 as a precursor to competing the bird 22, such as in races.

Referring with particularity to FIG. 7A, in a first step 705 (falcon selection and bonding), the bird 22 is selected, such as by a falconer, trainer or other individual 300. In a second step 710 (basic flight training), the bird 22 is taught to follow various parts of a telwah regimen. In a third step 715 (stamina building and distance training), the bird 22 becomes acclimated to increasingly longer distances, particular environments or the like. In a fourth step 720 (speed enhancement and ground flight training), the bird 22 is exposed to increasingly intense training regimens. In a fifth step 725 (desensitize with race equipment), the bird 22 is exposed to gates that make up the course 500, as well as to distractions from LIDAR or other visually disruptive mechanisms. In a sixth step 730 (evaluation and time trials), the bird 22 is timed to provide quantitative indicia of its performance.

Referring with particularity to FIG. 7B, and in a manner generally similar to that which takes place in FIG. 6B, the data that was acquired by the electronic device 100 during a data acquisition step 735 may be subjected to a first processing step 740 to determine under, an effectiveness step 745, how performance metrics 570 of FIG. 5B of the bird 22 that was trained under the regimen of FIG. 7A may be updated. This output is then subjected to a second processing step 750 so that under a feedback and continuous training step 755 adjustments to the training regimen the bird 22 may be effected. In step 760, various forms of software-implemented ways of conveying one or more of data, diagnostics and predictive analytics to the individual 300 or other interested party (such as through various communication protocols discussed herein).

Falconry Competition Data (FCD) includes the following types of specific data and/or other data as may be agreed by organizations that organize falconry competitions. The following are some examples which may be found in news reports or other sources on the internet, the time to complete a 400 meter race course, the loss of one point for each minute exceeding 20 minutes to complete the flight with pre-determined bird tasks (tasks may include Mounting (maximum flight speed attained by the bird prior to beginning its 'free-fall pursuit of a target' [Stoop]—there is affixed set of points for first place with lower points, ratioed to the highest, for other place positions), Pitch (the maximum height attained by the bird just prior to the release of the target.—there is affixed set of points for first place with lower points, ratioed to the highest, for other place positions), Stoop, and Pursuit (with each of the last two metrics having a unique algorithm for achieving points). Thus, FCD may be described as types of performance metrics 570 related specifically to races and other forms of competition. Specifically, FCD are output data to be used to be used in developing a supervised ML model which after deployment will predict FCD, such as through its trained inference engine. In one form, once the ML model is deployed, it can be used with Monte Carlo methods applied to the input data to optimize the FCD (for example, the time it takes to complete a 400 meter race) or to guide the development of training regimes. By way of example, the time it takes to complete one lap of a 400 meter track, course or race may be one form of the aforementioned performance metrics 570.

Figure 8A:
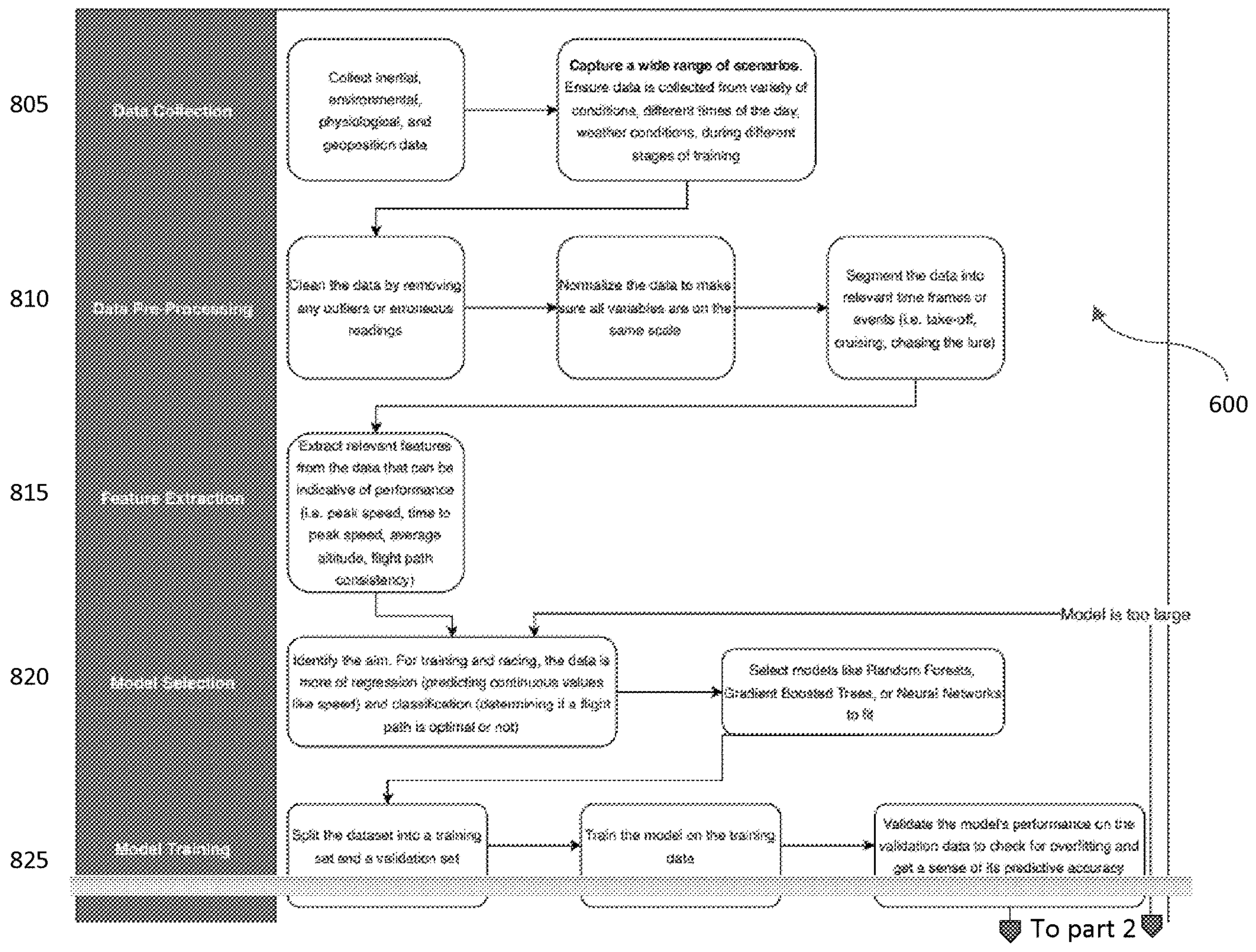
FIGS. 8A and 8B depict a program structure in the form of a flow diagram of how to develop an embedded, edge-based machine learning model for according to one or more embodiments shown or described herein.
Figure 8B:
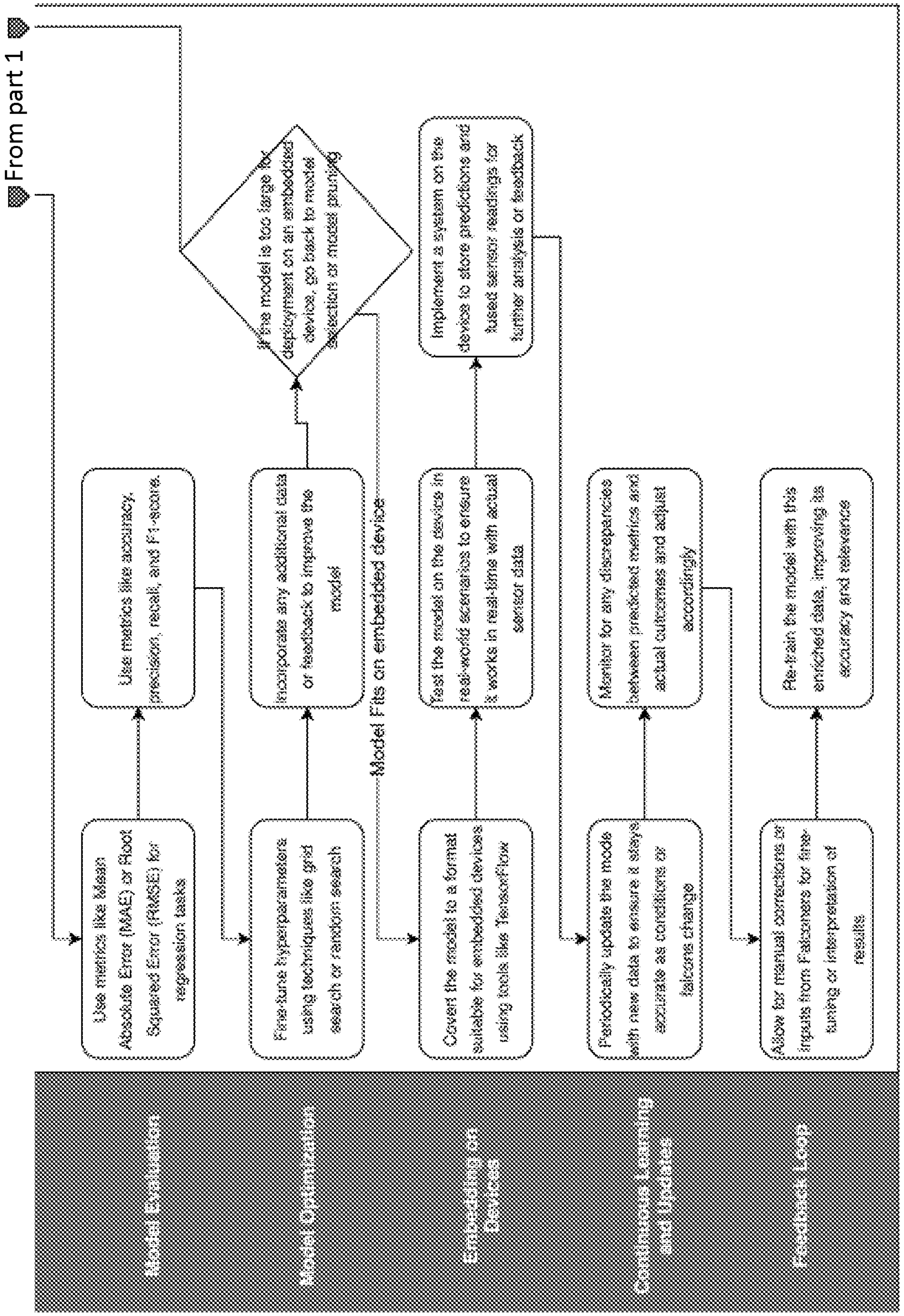

Referring next to FIGS. 8A and 8B, the ML model 800 may be used to develop and analyze the performance metrics 570. In one form, the electronic device 100 may be used as a predictive analytics platform that employs the ML model 800 as an edge-based embedded model to discern patterns and trends related to the performance and health of the bird 22. Regardless of whether the ML model 800 is developed and run at the edge that corresponds to the electronic device 100 or elsewhere within the operations center 200, base station 210, portable device 220, cloud 230, servers 240 or other part of the bird training and optimization system 1, it can provide one or both of predictive and descriptive analytics of performance metrics 570 related to the airborne object 20 in general and of the bird 22 in particular.

In a first step 805, raw data (such as flight data 550) is collected. In a second step 810, the collected data is preprocessed. In a third step 815, one or more relevant features are extracted. In a fourth step 820, a model selection takes place to identify the event in question (for example, racing or training). In a fifth step 825, a model training takes place. In some forms, the fourth and fifth steps 820, 825 may be combined as part of a larger model training operation. In a sixth step 830, a model evaluation takes place to assess the accuracy or other metric related to the fifth step 825. In a seventh step 835, a model optimization takes place in order to fine-tune hyperparameters. In an eighth step 840, the trained, optimized model may be converted into a format suitable for use on the electronic device 100 (regardless of whether one or more of the first through seventh steps are performed on the electronic device 100 or elsewhere within the bird training and optimization system 1. At this point, the trained, optimized model becomes the ML model 800. In a ninth step 845, continuous learning and updates to the ML model 800 may be undertaken to ensure that it is performing correctly. In a tenth step 850, a feedback loop may be added to re-train or make other corrections to the ML model 800. Thus, in these latter steps, new inference data (that is, real-time data associated with bird 22 training, racing or other data-gathering activity) is added to a data lake (or otherwise input as part of the data collecting first step 805) as part of analytics-based updates to the ML model 800. The analytic updates themselves may perform some of all of the previous steps (including those for preprocessing, model prediction and post-processing).

In one form, the data being acquired (such as the IMU $S_1$ data of FIG. 4, for example) by one or more of the electronic device 100 of and sensors S of FIGS. 2 and 3 may be placed within the data lake (not shown) that may form a part of the data collection of the first step 805. Likewise, the various preprocessing activities that may take place within the second step 810 may be used to ensure that the data is internally consistent; such preprocessing may include transformation, exploration, normalization, standardization, consolidation, among others as a way to improve data optimization and evaluation that takes place in the subsequent feature engineering of the third step 815 where one or both of the preprocessing and feature engineering steps may further involve exploration and labeling of the data as a way to have it be formatted. In one form, various mapping procedures may be used to ensure suitable correlation of the data. The resulting mapped data thereby allows a measure of sensor-agnostic (that is to say, independent of the sensor S domain) acquisition of the data, regardless of semantics, formatting or other vagaries of each data form. This in turn permits other parts of the architecture (including the software that are otherwise sensor-aware such that communication between the electronic device 100 and the sensors S using a protocol that is native to each respective sensor S) to be sensor-agnostic. Subsystems or components that may be used to promote such a sensor-agnostic architecture include a resource scheduler and allocator (RSA), a sensor controller (SC) providing an application programming interface for utilizing the plurality of resources allocated by the RSA, a signal-processing subsystem manager (SP SSM) configured to manage a plurality of signal-processing resources by interfacing with the RSA and the SC and by communicating with one or more signal-processing nodes utilizing the plurality of signal-processing resources. Within the present context, the use of a sensor-agnostic detection and recognition system (such as that based on the electronic device 100) for the bird 22 or other airborne object 20 of interest) may include various modules for data normalization, standardization, mapping, feature extraction and related activities in order to perform the one or more identification, location-determining or other functions related to the use of the flight data 550 described herein. Thus, by rendering the data into a form that is acquired from disparate sources into a form that is more uniform, subsequent computational workload (such as feature extraction, training or the like) is greatly reduced. This significantly improves the operation of the electronic device 100, especially when used as an edge computing device within a communication network as described herein, even more particularly when the edge-based electronic device 100 generates predictive analytics or based on the ML model 800. In one form, the extracted features may be stored in a feature map.

Semantic features may be used as part of a lakehouse architecture as a way to—through a suitably-configured abstraction layer—ensure analytic functionality and multi-platform compatibility and integration of large data sets, especially when coupled with relational databases such as those that may use structured query language (SQL) or related languages. In one form, combining SQL and a lakehouse architecture can provide massive parallel processing functionality for rapid analytics on data lakes, as well as direct file access for ML model 800 including for situations where an SQL-based data warehouse is not needed.

In one form, the ML model 800 may represent a decision support engine that can provide heuristic reasoning for a trainer, clinician or other user or individual that is interested in rapidly and relatively easily understanding the relationship between one or more performance metrics 570 of the bird 22 and its health or ability to participate in an activity. Such a model 800 may be based on numerous forms of input data, including that which is used to monitor and detect physical and behavioral signs, whether in quantitative and qualitative form. As previously noted, examples of such signs may include stress, fear, frustration, overheating or exhaustion, among others. For example, birds 22 in general (falcons in particular) under stress may exhibit panting, head shaking or tail twitching. They may also have a higher heart rate and cortisol levels. In such case, one metric in general and a performance metric 570 or measure in particular) could be to measure the time to the onset of stress. Likewise, a fearful falcon may have a lower body posture, and may be more timid or avoidant of certain situations or stimuli. Similarly, a falcon experiencing frustration may exhibit restlessness, feather-ruffling or vocalizations. Relatedly, a falcon that is overheated may pant excessively, have a faster heart rate or have dilated pupils. In one form, the ML model 800 can aggregate one or more of observational data 560, sensor S data and geoposition data (which itself may form part of the aforementioned flight data 550), in order to not just track changes in the physical and cognitive health of the bird 22, but also to provide predictions of how such changes may be improved, avoided or maintained depending on what performance metric 570 is being sought.

As previously noted, biomarkers can provide indicia of bird 22 behavior such as stress, fear, frustration or overheating. Within the present context, biomarkers are biological markers that refer to measurable indicators of a biological state or condition. As such, they are objective and quantifiable characteristics of biological processes. Biomarkers can be molecules, genes, gene products, enzymes or hormones. They might indicate either normal or pathogenic processes or pharmacological responses to a therapeutic intervention. Relatedly, physiological data is that which represents the normal functions or activities of a living organism. As previously noted, examples include measurements of parameters such as heart rate, blood pressure, respiratory rate, body temperature or the like. This data reflects the body's functional states and can change in response to various factors such as stress, exercise, or illness.

It will be appreciated that the biomarkers themselves may constitute either dependent or independent variables. For example, certain bird 22 movements, behavior or disposition that is indicative of such stress, fear, frustration or overheating may be directly observed (such as by the trainer, owner, medical personnel or the like), while in another form inferred based on an algorithmic determination based on one or more forms of data from the sensors S. Relatedly, while the data being acquired from the sensors S in general and the physiological sensors $S_3$ in particular are independent, information derived therefrom (such as a certain performance metric 570) is dependent. In one form, and as with the trainer observational data 560, the sensed data from the physiological sensors $S_3$ (possibly in conjunction with the sensed data from one or both of the IMU $S_1$ and environmental sensors $S_2$) may act as either a dependent or independent form of biomarker data. Thus, in one form, the training regimen data of the bird 22 is considered to be independent data.

As previously mentioned, data may be qualitative or quantitative; depending on the nature of the biomarker data, it too can be one or the other type. For example, biological data may include that related to behavior, health or direction and spatial awareness. Behavior data may be based on pattern recognition of the motion of the bird 22 when flying or on the ground. Likewise, health information may be derived from noticing biomarkers or other leading indicators. Relatedly, direction and spatial awareness may include the detection of head, neck, chest or other parts of the body movements to indicate directional intent; this in turn may be used to quantify bird 22 navigation.

Figure 9:
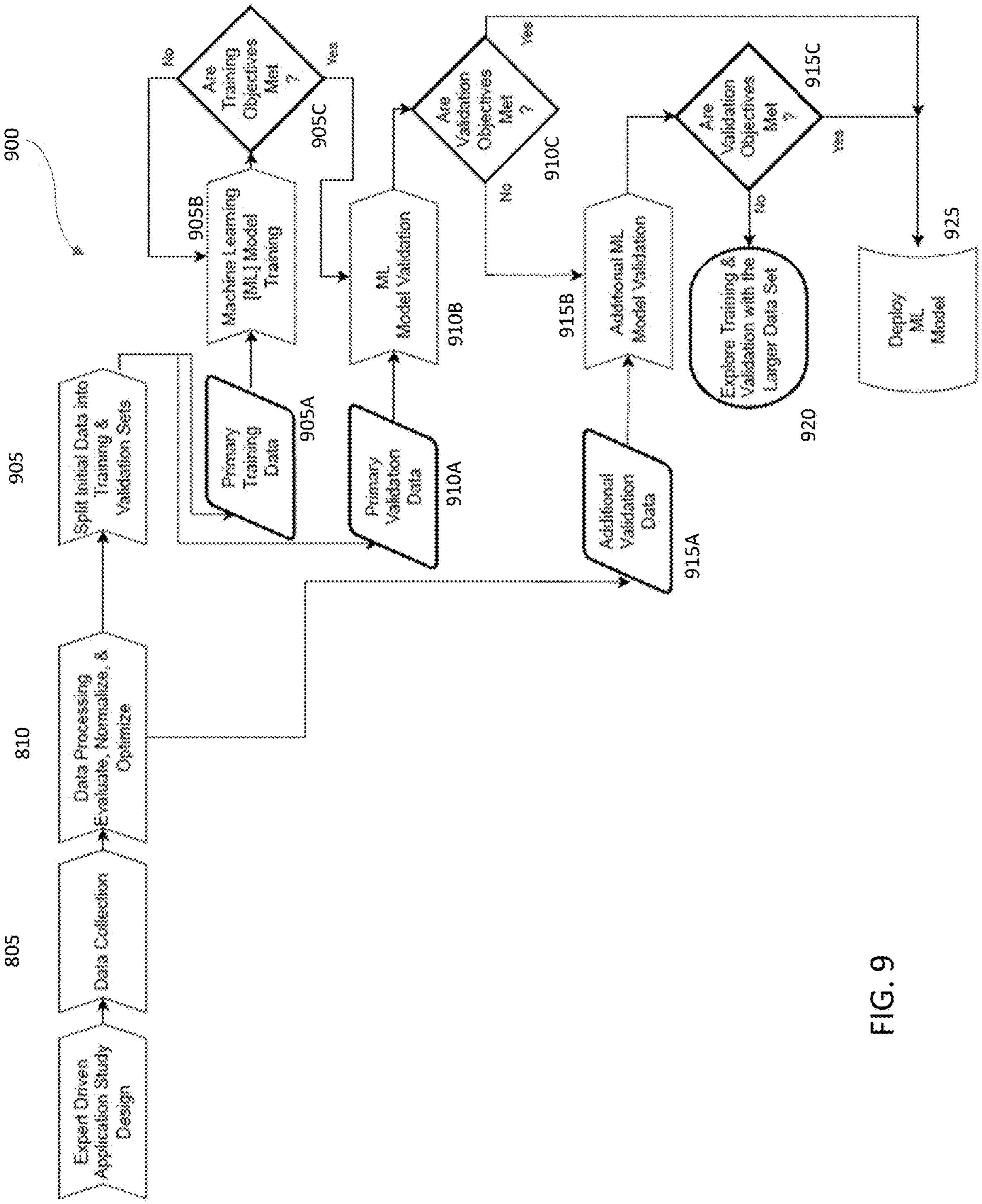
FIG. 9 depicts a program structure in the form of a flow diagram of how to convert various forms of acquired data into a performance metric of the bird of FIG. 1.

Referring next to FIG. 9 in conjunction with FIGS. 8A and 8B, a flowchart 900 depicting how one form of how at least the first through eighth steps 805 through 840 of producing the ML model 800 takes place. As can be seen, data that has been subjected to the preprocessing and feature extraction of the second and third steps 810, 815 may be spilt into numerous data sets for training 905 and validation 910. For example, a primary training set 905A and a primary validation (or testing) data set 910A may be separated from one another so that respective training 905B and validation 910B may take place. A loop-based training decision point 905C may be used to determine when the building of the ML model 800 transitions from the training 905 to the validation 910. A loop-based validation decision point 910C may be used to determine when validation objectives have been met. For example, in situations where such objectives are not met, a secondary validation data set 915A may be selected from one or both of the preprocessing and feature extraction of the second and third steps 810, 815. By way of example, this may employ cross-validation or other forms of model generalization activities such as to reduce (or at least balance) variance and bias. In cases where needed, the secondary validation data set 915A may be subjected to additional model validation 915B after which another loop-based training decision point 915C may be used to determine when validation objectives have been met in a manner generally similar to the loop-based validation decision point 910C. If the objectives are not met, more data 920 may be used to explore additional training and opportunities in a manner generally similar to the foregoing. Otherwise, once the objectives have been met, the ML model 800 may be deployed 925 for use, whether at the edge, backhaul or a combination of both.

Within the present disclosure, it will be understood that the operations, functions, logical blocks, modules, circuits, and algorithm or model steps or events described may be implemented in hardware, software, firmware or any combination thereof. Moreover, if implemented in software, such operations may be stored on or transmitted over as one or more instructions or code on the aforementioned computer-readable medium. The steps or events of a method, algorithm or ensuing model disclosed herein may be embodied in a processor-executable software module, which may reside on a tangible, non-transitory version of such computer-readable medium such that the medium be in any available form that permits access to the events or steps by a processor or related part of a computer. By way of example, and not limitation, such non-transitory computer-readable medium may comprise RAM, ROM, EEPROM, CD-ROM or other optical disk storage, magnetic disk storage or other magnetic storage devices, flash memory or any other form that may be used to store desired program code in the form of instructions or data structures and that may be accessed by a processor or related part of a computer. Combinations of the above should also be included within the scope of non-transitory computer-readable media. Additionally, the operations of a method, algorithm or model may reside as one or any combination or set of codes or instructions on a tangible, non-transitory machine readable medium or computer readable medium, which may be incorporated into a computer program product. Furthermore, in one non-limiting form. upon having the program code means loaded into memory in general (and in one form into ROM in particular), the processor, microprocessor, controller, microcontroller, SoC or related computational device becomes a specific-purpose machine configured to perform the various computational tasks described herein. In this way, the associated computer becomes a particularly-adapted computer or computer-related data processing device that possesses particular capabilities tied to the resulting instruction set architecture.

Within the present disclosure, one or more of the following claims may utilize the term "wherein" as a transitional phrase. For the purposes of defining features discussed in the present disclosure, this term is introduced in the claims as an open-ended transitional phrase that is used to introduce a recitation of a series of characteristics of the structure and should be interpreted in like manner as the more commonly used open-ended preamble term "comprising" and its variants that do not preclude the possibility of additional acts or structures.

Within the present disclosure, terms such as "preferably", "generally" and "typically" are not utilized to limit the scope of the claims or to imply that certain features are critical, essential, or even important to the disclosed structures or functions. Rather, these terms are merely intended to highlight alternative or additional features that may or may not be utilized in a particular embodiment of the disclosed subject matter. Likewise, it is noted that the terms "substantially" and "approximately" and their variants are utilized to represent the inherent degree of uncertainty that may be attributed to any quantitative comparison, value, measurement or other representation. As such, use of these terms represents the degree by which a quantitative representation may vary from a stated reference without resulting in a change in the basic function of the subject matter at issue.

Within the present disclosure, the use of the prepositional phrase "at least one of" is deemed to be an open-ended expression that has both conjunctive and disjunctive attributes. For example, a claim that states "at least one of A, B and C" (where A, B and C are definite or indefinite articles that are the referents of the prepositional phrase) means A alone, B alone, C alone, A and B together, A and C together, B and C together, or A, B and C together. By way of example within the present disclosure, if a claim recites that data is being acquired from at least one of a first sensor, a second sensor and a third sensor, and if such data is being acquired from the first sensor alone, the second sensor alone, the third sensor alone or any combination of the first, second and third sensors, then such data acquisition satisfies the claim.

Within the present disclosure, the following claims are not intended to be interpreted based on 35 USC 112(f) unless and until such claim limitations expressly use the phrase "means for" or "steps for" followed by a statement of function void of further structure. Moreover, the corresponding structures, materials, acts and equivalents of all means or step plus function elements in the claims that follow are intended to include any structure, material or act for performing the function in combination with other claimed elements as specifically claimed.

Within the present disclosure, the singular forms "a," "an" and "the" include plural references unless the context clearly dictates otherwise. The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9 to 1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6 to 9, the numbers 7 and 8 are contemplated in addition to 6 and 9, and for the range 6.0 to 7.0, the number 6.0, 6.1, 6.2, 6.3, 6.4, 6.5, 6.6, 6.7, 6.8, 6.9 and 7.0 are explicitly contemplated.

Having described the subject matter of the present disclosure in detail and by reference to specific embodiments, it is noted that the various details disclosed in the present disclosure should not be taken to imply that these details relate to elements that are essential components of the various described embodiments, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure may be identified as preferred or particularly advantageous, it is contemplated that the present disclosure is not necessarily limited to these aspects.

It will be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

What is claimed is:

1. A method for assessing a bird, the method comprising:
configuring an electronic device to be attached to the bird, the electronic device comprising a microcontroller and a communication module that cooperate together to:
acquire, from a plurality of sensors, at least one of inertial data, environmental data and bird physiological data; and
acquire bird geoposition data from at least one of a terrestrial system and an extraterrestrial system;
upon allowing the bird to become airborne, operating the electronic device to convert the acquired at least one of inertial, environmental, bird physiological and bird geoposition data into flight data of the airborne bird;
acquiring observational data about the bird;
using the communication module to exchange the flight data and the observational data between the electronic device and an operations center over a communication network; and
analyzing at least one performance metric of the bird based the exchanged flight data and observational data.

2. The method of claim 1, wherein the communication network comprises a low power wide area network.

3. The method of claim 2, wherein the low-power wide area network operates over a LoRa-based protocol.

4. The method of claim 2, wherein the communication module comprises a hybrid communication module comprising:
a first sub-module that acquires at least one of the inertial data, environmental data and bird physiological data from the plurality of sensors;
a second sub-module that acquires the bird geoposition data from the global navigation satellite system; and
a third sub-module that transmits the flight data over the low power wide area network.

5. The method of claim 1, wherein the analyzing takes place on the electronic device.

6. The method of claim 1, wherein the observational data comprises at least one general metric of the bird.

7. The method of claim 6, wherein the at least one general metric of the bird comprises at least one behavioral or physiological state of the bird.

8. The method of claim 7, wherein the at least one behavioral or physiological state of the bird comprises a bird species, age of the bird, at least one prior training regimen, diet of the bird, health metrics of the bird, weather conditions at the time of observation, migration pattern of the bird, social interaction of the bird, mating habits of the bird, nesting behavior of the bird, foraging strategy of the bird and combinations thereof.

9. The method of claim 1, wherein the allowing the bird to become airborne comprises subjecting the bird to at least one of a training regimen and a competition regime.

10. The method of claim 1, wherein the analyzing at least one performance metric of the bird based the exchanged flight data and observational data comprises fusing at least a portion of at least one of the acquired inertial, bird geoposition, environmental, bird physiological and observational data using a time series analysis.

11. The method of claim 1, further comprising presenting the flight data to an individual by mapping a visual representation of the flight data onto a visualization device.

12. The method of claim 1, wherein the microcontroller defines an edge processing platform with which to generate the flight data.

13. The method of claim 1, further comprising using real-time kinematics to refine the acquired bird geoposition data.

14. The method of claim 1, wherein the bird geoposition data is acquired from a global navigation satellite system.

15. The method of claim 1, wherein the bird geoposition data is acquired from at least one of a real-time kinematics system, a mobile telephone and a beacon.

16. A system for performing data-informed analysis of a bird, the system comprising:
an operations center; and
an electronic device in signal communication with the operations center, the electronic device comprising a microcontroller and a communication module that cooperate together such that when secured to a bird acquires bird physiological data and at least one of inertial data, environmental data, bird geoposition data and observational behavior, the communication module comprising:
a first sub-module that acquires the inertial data from a plurality of sensors;
a second sub-module that acquires the observational data from the operations center and the bird geoposition data from at least one of an extraterrestrial system and a terrestrial system; and
a third sub-module that transmits flight data over a low power wide area network to the operations center.

17. A machine learning-based system for analyzing a flight path of a bird, the system comprising:
a plurality of sensors comprising an inertial measurement unit, at least one physiological sensor and at least one environmental sensor;
a communication module configured to operate using a plurality of modes of communication one of which comprises a low power wide area network; and
at least one microcontroller signally cooperative with the plurality of sensors and the communication module to exchange information therebetween, the at least one microcontroller comprising at least one processor and a non-transitory computer-readable medium storing machine-readable instructions that cause the at least one processor to:
acquire first sensor data from the inertial measurement unit, second sensor data from the at least one physiological sensor and third sensor data from the at least one environmental sensor;
acquire, using the communication module, location data from at least one of a terrestrial system and an extraterrestrial system;
using a trained machine learning model that correlates the acquired sensor and location data to determine at least one performance metric of the bird, and
transmit, using at least the low power wide area network portion of the communication module, the determined at least one performance metric to a user.

18. The machine learning-based system of claim 17, wherein the machine-readable instructions further cause the at least one processor to acquire observational data from the user that is in wireless signal communication with the communication module.

19. The machine learning-based system of claim 18, wherein the instructions, when executed by the at least one processor, further cause the at least one processor to use at least one machine learning algorithm to train and update, based on the acquired observational data, the acquired sensor data and the acquired location data, the model to classify a physical activity of the bird.

20. The machine learning-based system of claim 19, wherein the bird is a bird of prey.

* * * * *